(12) United States Patent
Worden et al.

(10) Patent No.: US 9,714,404 B2
(45) Date of Patent: Jul. 25, 2017

(54) CATALYTIC BIOREACTORS AND METHODS OF USING SAME

(71) Applicant: BOARD OF TRUSTEES OF MICHIGAN STATE UNIVERSITY, East Lansing, MI (US)

(72) Inventors: Robert Mark Worden, Holt, MI (US); Yangmu Chloe Liu, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 358 days.

(21) Appl. No.: 14/199,714

(22) Filed: Mar. 6, 2014

(65) Prior Publication Data

US 2014/0187826 A1   Jul. 3, 2014

Related U.S. Application Data

(63) Continuation-in-part of application No. PCT/US2012/053958, filed on Sep. 6, 2012.
(Continued)

(51) Int. Cl.
*C12M 1/00*    (2006.01)
*C12M 1/12*    (2006.01)
*C12P 7/16*    (2006.01)

(52) U.S. Cl.
CPC ............ *C12M 21/12* (2013.01); *C12M 23/34* (2013.01); *C12M 25/12* (2013.01); *C12P 7/16* (2013.01); *Y02E 50/10* (2013.01)

(58) Field of Classification Search
CPC ...... C12M 21/12; C12M 23/34; C12M 25/12; C12P 7/16; Y02E 50/10; Y02E 60/50;
(Continued)

(56) References Cited

U.S. PATENT DOCUMENTS 4,524,137 A   6/1985   Hagerdal et al.
6,409,976 B1  6/2002   Poschmann et al.
(Continued)

FOREIGN PATENT DOCUMENTS

WO   2004/056455 A1   7/2004
WO   2013/036635 A1   3/2013

OTHER PUBLICATIONS

International Search Report and Written Opinion received for PCT Patent Application No. PCT/US2012/053958, mailed on Feb. 7, 2013, 8 pages.
(Continued)

*Primary Examiner* — Michael Hobbs
(74) *Attorney, Agent, or Firm* — Clark IP Law, PLC

(57) ABSTRACT

Various embodiments provide a bioreactor for producing a bioproduct comprising one or more catalytically active zones located in a housing and adapted to keep two incompatible gaseous reactants separated when in a gas phase, wherein each of the one or more catalytically active zones may comprise a catalytic component retainer and a catalytic component retained within and/or thereon. Each of the catalytically active zones may additionally or alternatively comprise a liquid medium located on either side of the catalytic component retainer. Catalytic component may include a microbial cell culture located within and/or on the catalytic component retainer, a suspended catalytic component suspended in the liquid medium, or a combination thereof. Methods of using various embodiments of the bioreactor to produce a bioproduct, such as isobutanol, are also provided.

25 Claims, 19 Drawing Sheets

Related U.S. Application Data

(60) Provisional application No. 61/531,304, filed on Sep. 6, 2011.

(58) Field of Classification Search
CPC . B01J 8/009; B01J 8/02; B01J 19/2475; B01J 2208/00336; B01J 2208/00407; B01J 2219/00132; C01B 3/323; C01B 3/201; C01B 3/203; C01B 2203/041; H01M 8/0631
See application file for complete search history.

(56) References Cited

U.S. PATENT DOCUMENTS

2003/0022364 A1    1/2003  Parent et al.
2009/0104676 A1*  4/2009  Tsai ...................... C12M 21/12
                                                                          435/161

OTHER PUBLICATIONS

Chen et al., "Model-Based Flow Property Estimation Using an Ionic Polymer-Metal Composite Beam", Preprint submitted to 4th Annual Dynamic Systems and Control Conference, Received Mar. 19, 2011, 2011, 8 pages.

Maiti et al., "Continuous Isobutanol Production in a Bioreactor for Incompatible Gases", Sustainable Engineering Forum, AIChE Annual Meeting, Nov. 3-8, 2013, pp. 1-28.

Maiti et al., "In-situ Isobutanol Recovery from an Autotrophic Fermentation in a Bioreactor for Incompatible Gases", Sustainable Engineering Forum, AIChE Annual Meeting, Nov. 6, 2013, pp. 1-19.

Worden, "Process Development Issues in Electrofuels Fermentations", CHEMS Research Forum, Michigan State University, May 9, 2013, pp. 1-69.

* cited by examiner

CATALYTIC BIOREACTORS AND METHODS OF USING SAME

RELATED APPLICATIONS

This application is a continuation-in-part under 35 U.S.C. 111(a) of International Application No. PCT/US2012/053958, which application was filed on Sep. 6, 2012 and published in English as WO 2013/036635 on Mar. 14, 2013, which application claims the benefit under 35 U.S.C. 119(e) of U.S. Provisional Application Ser. No. 61/531,304, filed on Sep. 6, 2011, which applications and publication are hereby incorporated by reference in their entireties.

STATEMENT OF GOVERNMENT RIGHTS

This invention was made with government support under DE-AR0000056 awarded by the U.S. Department of Energy. The government has certain rights in the invention.

BACKGROUND

Catalytic reactors are vessels used to contain and catalyze chemical reactions in a manner to maximize net value or yield for a given reaction. However, many conventional catalytic reactors are undesirable for chemical reactions between gaseous components that are incompatible when mixed as gases.

SUMMARY

In one embodiment, a bioreactor for producing a bioproduct is provided comprising a housing; and one or more catalytically active zones located in the housing and adapted to keep two incompatible gaseous reactants separated when in the gas phase, wherein each of said catalytically active zones comprises a catalytic component retainer and a catalytic component retained within and/or on the catalytic component retainer. In one embodiment, each of said catalytically active zones additionally or alternatively comprise a liquid medium located on either side of the catalytic component retainer and the catalytic component additionally or alternatively includes a suspended catalytic component suspended in the liquid medium, such that the liquid medium is a catalytically active zone.

Various embodiments further provide for methods of making bioproducts with the bioreactor, such as biofuel (e.g., isobutanol), from $H_2$ and $CO_2$. In one embodiment, the $H_2$ is solar-derived and use of $CO_2$ as a carbon source provides a method for consuming greenhouse gases.

DETAILED DESCRIPTION OF THE EMBODIMENTS

Figure 1:
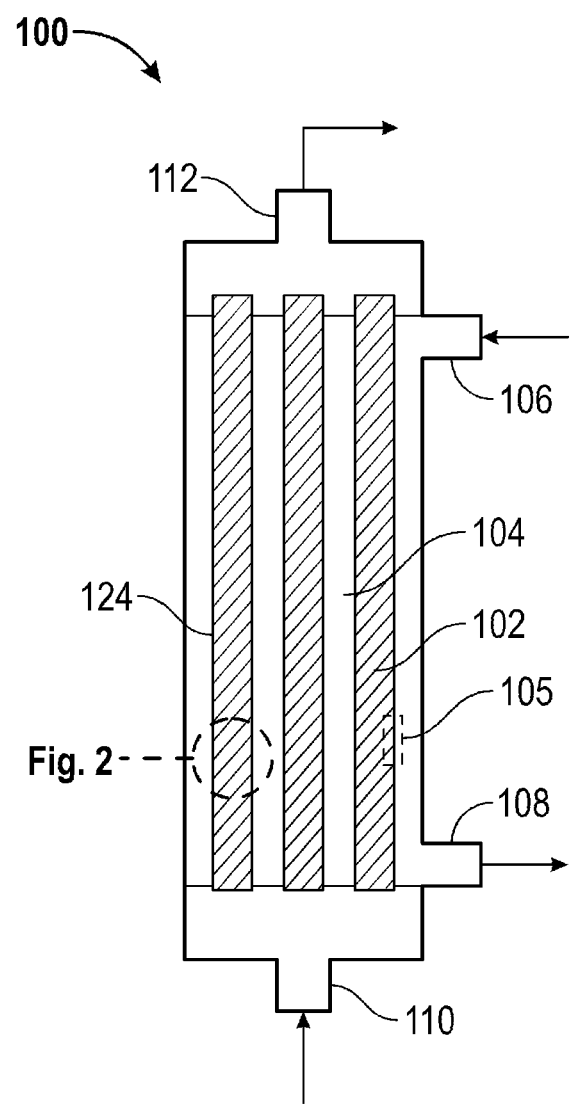
FIG. 1 is a schematic illustration of a bioreactor according to an embodiment.

In the following detailed description, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of embodiments of the present invention is defined only by the appended claims.

The embodiments described herein include a bioreactor capable of biological conversion of incompatible gaseous reactants, such as gases that, when mixed in the gas phase can explode or erupt in fire in the presence of an ignition source. The incompatible gaseous reactants may be soluble, insoluble or sparingly soluble in a medium (e.g., liquid), in which a catalytic component is grown. In one embodiment, the incompatible gaseous reactants have low solubility in aqueous phase, i.e., "low aqueous solubility." In one embodiment, the incompatible gaseous reactants are hydrogen ($H_2$) and oxygen ($O_2$), which, together with carbon dioxide ($CO_2$), are capable of being converted by the catalytic component to IBT. Various embodiments further include methods of producing bioproducts using a bioreactor, such as a hollow fiber bioreactor.

The term "bioreactor" as used herein refers to a device that contains a catalytic component within which gaseous components, including incompatible gaseous reactants, can be converted into one or more bioproducts.

The term "bioproduct" as used herein refers to a biochemical or biofuel.

The term "biofuel" as used herein refers to any renewable solid, liquid or gaseous fuel produced from biologically derived feedstocks and/or using biologically derived catalysts, for example, those derived from biomass. Most biofuels are originally derived from biological processes such as the photosynthesis and can therefore be considered a solar energy derived chemical energy source.

The term "catalytic component retainer" as used herein refers to a porous material having pores of one or more sizes and which is capable of retaining a liquid medium on one side. The catalytic component retainer is also capable of retaining a catalytic component, such as by embedding the catalytic component within the pores and/or binding it to a surface without entering the pores and/or by retaining it on the side of the catalytic component retainer which contains the liquid medium. Once retained, the catalytic component retainer allows growth of an amount of catalytic component within and/or thereon and/or on the side containing the liquid medium. A catalytic component retainer can take many forms, including, but not limited to, a substrate, such as a hollow fiber or a substantially flat, planar surface.

The term "catalytic component" as used herein refers to a component capable of catalyzing a chemical reaction. The catalytic component can be located on and/or in and/or on the side of a catalytic component retainer containing a liquid medium. Once retained, the catalytic component can be grown on and/or in and/or on the side of the catalytic component retainer containing a liquid medium from a culture containing one or more type of bacteria.

The term "catalytically active zone" as used herein refers to a location within the bioreactor in which a catalytic component may be grown. A catalytically active zone can comprise a catalytic component retainer and a catalytic component. A catalytically active zone can additionally or alternatively comprise a liquid medium containing suspended (planktonic) cells, wherein the liquid medium is located on either side of the catalytic component retainer.

The term "hollow fiber" or "hollow tube" as used herein refers to a catalytic component retainer having a substantially annular shape and comprising a porous fiber wall that surrounds an open core (i.e., lumen) through which fluids (gas and/or liquid) can flow. The term "tube" as used herein is intended to refer to a "hollow tube."

The term "lumen side" as used herein refers to an inner side of a hollow tube. This is in contrast to a "shell side" which is intended to refer to an outer side of a hollow tube.

The term "porous fiber wall" or "fiber wall" as used herein refers to a membrane, i.e., wall, of a hollow fiber having pores of one or more designated sizes and which is capable of retaining, and, if applicable, growing an amount of catalytic component within and/or on an inner surface and/or on an outer surface. The outer and/or inner surfaces of some types of fiber walls may comprise a "skin layer," i.e., a layer having pores of a designated pore size distribution which are generally smaller in size as compared with pores within the rest of the fiber wall. Some fiber walls may alternatively or additionally comprise a "porous matrix" or "spongy layer" within the fiber wall, i.e., a supporting layer having pores larger than a designated pore size and generally larger in size as compared with pores in the skin layer.

The term "biofilm" as used herein refers to a catalytic component having a substantially continuous form either on an inner and/or outer surface of a catalytic component retainer or within pores of a catalytic component retainer.

The term "inoculation" as used herein refers to a process that introduces a catalytic component onto and/or within a liquid or solid substance.

The term "filtration" or "filtration-type inoculation" as used herein refers to a method which relies on hydrostatic pressure to inoculate a catalytic component retainer, such as a hollow fiber, with cells (e.g., bacteria) from a culture, such as a liquid culture, onto and/or into a catalytic component retainer, such as a hollow tube. When the catalytic component retainer is a hollow fiber, the filtration can be performed by forcing liquid in the liquid culture to flow outwardly from a lumen side of a hollow fiber through pores in the porous fiber wall ("inside-out") or by using a pressure difference across the porous fiber wall to force liquid in the liquid culture to flow inwardly from outside the porous fiber wall of the hollow fiber through to a lumen side ("outside-in"). In either case, some fraction of the cells in the liquid culture may be too large to pass through pores in the porous fiber wall and would therefore be deposited on and/or within the porous fiber wall.

The term "incubation" or "incubation-type inoculation" as used herein refers to a method of inoculating a catalytic component retainer with cells from a fluid culture (e.g., gas or liquid) without the use of pressure differences to force liquid through a catalytic component retainer. This method can be performed by contacting a culture containing cells to be inoculated with the catalytic component retainer and then incubating the catalytic component retainer with the culture (i.e., keeping the catalytic component retainer in contact with the culture) for some desired period of time. When the catalytic component retainer is a hollow fiber, incubation-type inoculation can be achieved by delivering a liquid culture into a lumen side of a hollow fiber and/or by exposing the outside of a hollow fiber to a reservoir of liquid culture. Although not intended with this method, it is possible that exposure to a reservoir of a liquid culture can also allow some liquid culture to flow outwardly, at least initially.

The term "incompatible gaseous reactants" as used herein refers to gaseous components which are chemically incompatible and, as such, do not produce a desired product readily, safely and/or efficiently. Incompatible gaseous reactants can be explosive in gaseous form. Incompatible gaseous reactants can also produce undesired chemical reactions, thus reducing bioproduct yield in a bioreactor.

The term "transport" as used herein refers to movement of a component into and/or across a porous fiber wall. Transport can occur by convection or diffusion.

The term "diffusion" as used herein refers to net transport of a transferred species via random molecular movement in the absence of bulk fluid movement. Diffusion occurs in the direction of a spatial concentration gradient of the transferred species.

The term "convection" as used herein refers to transport via bulk movement of a fluid into and/or across a porous fiber wall. Convection occurs in the direction of the bulk fluid movement.

The term "flux" as used herein refers to a rate of movement of a component through a porous barrier normalized per unit cross-sectional area of the porous barrier.

The term "dissolve" as used herein refers to solubilization of a gas in a liquid. The dissolution can be partial or complete.

The term "insoluble" as used herein refers to a solubility of a gas in a liquid of less than 0.1 g per 100 ml.

The term "soluble" as used herein refers to a solubility of a gas in a liquid of greater than 1 g per 100 ml.

The term "sparingly soluble" as used herein refers to a solubility of a gas in a liquid of between about 0.1 g per 100 ml and about 1 g per 100 ml.

The term "low solubility" as used herein encompasses both "sparingly soluble" and "insoluble." As such, low solubility components include both insoluble gaseous components and sparingly soluble gaseous components.

The term "medium" as used herein refers to a carrier capable of containing components and/or dissolving one or more incompatible gaseous reactants therein. A medium may be a liquid or a gas.

The term "autotrophic production medium" as used herein refers to a medium capable not only of containing components but also of dissolving one or more gaseous components, namely incompatible gaseous reactants, therein. Some components contained in the autotrophic production medium are conducive to a chemical reaction by the catalytic component to produce a bioproduct.

The term "culture" as used herein refers to a catalytic component (e.g., cell) and its carrier. When the carrier is a liquid, the culture is referred to as a "liquid culture."

The term "liquid phase" as used herein refers to either a bulk liquid or a solid phase containing a liquid.

The terms "continuous phase" and "dispersed phase" as used herein refer to a distribution of components in a mixture of two or more phases. A dispersed phase is subdivided into multiple, discrete portions (e.g., bubbles) that are physically separated from one another by a phase boundary. The discrete portions of the dispersed phase are immersed in a second phase (the continuous phase) that is not subdivided into discrete portions. The entire volume of the continuous phase is connected.

The term "continuous liquid phase" as used herein refers to a liquid phase that is not separated by phase boundaries into discrete portions.

The term "dispersed gas phase" as used herein refers to a gas phase that is separated by phase boundaries into discrete portions (e.g. bubbles) within a continuous liquid phase.

The term "carbon source" as used herein refers to a gaseous autotrophic carbon source (e.g., carbon dioxide, such as when hydrogen is an energy source) or a heterotrophic carbon source (e.g., fructose, which also functions as an energy source). An example electron acceptor for either the autotrophic or heterotrophic carbon source is oxygen.

The term "autotrophic" as used herein refers to a reaction that uses carbon dioxide as the carbon source.

The term "heterotrophic" as used herein refers to a reaction that uses a reactant other than carbon dioxide as the carbon source.

The term "reactant" as used herein refers to a component that is reactive.

The term "cell" as used herein refers to a living cell which can include a plant cell, animal cell or single celled organisms, i.e., microbial cell (e.g., bacterium).

The term "fermentation" as used herein refers to a chemical transformation process in which one or more reactants are converted into one or more products by the action of microorganisms.

Gas-phase mixtures of electron accepting gases and energy rich gases are considered to be incompatible gaseous reactants. Development of catalytic processes to convert incompatible gaseous reactants to products, such as bioproducts, has been challenging, because molecules of these reactants need to be brought into contact with a catalytic component, while mixing of the reactants in the gas phase can result in an undesirable trait that underlies the incompatibility (e.g., formation of an explosive gas mixture).

Previous attempts to mitigate such formations include mixing the incompatible gaseous reactants in proportions that reduce the incompatibility problem, by reducing the concentration of at least one of the incompatible gaseous reactants. However, such dilution can reduce the transport rate of that gaseous reactant phase to the liquid phase containing the catalytic component. This result occurs since a gaseous reactant's dissolution rate is roughly proportional to its concentration in the gas phase.

The bioreactors provided herein are capable of catalyzing chemical reactions between incompatible gaseous reactants which are incompatible when mixed in the gas phase, but which are compatible after being dissolved in a liquid phase or consumed by a catalytic component. As such, the systems and methods described herein address issues pertinent to, but not limited to, handling of explosively incompatible gaseous reactants and, in embodiments in which the gaseous components have low aqueous solubility, issues pertinent to rate-limiting gas mass transport.

In one embodiment, the bioreactors described herein include a series of catalytically active zones (i.e., catalytic partitions or catalytic barriers) adapted to keep incompatible gaseous reactants separated. In one embodiment, the catalytically active zone includes a fiber wall and a catalytic component contained within and/or on the fiber wall in a manner which allows a first gaseous reactant, such as a first incompatible gaseous reactant, contained in a medium (on a first side of the catalytically active zone) to be consumed by the catalytic component, and a second gaseous reactant (on an opposing side of the catalytically active zone) to also be substantially consumed by the catalytic component, and/or which dissolves in a medium contained in the catalytically active zone and diffuses through the catalytically active zone to the catalytic component where it is also substantially consumed.

As such, there is generally no bulk flow of liquid across the catalytically active zone in either direction, although, in one embodiment, a small amount of bulk flow may occur, such as when pressure perturbations are used. Most of the medium that enters a first side of the catalytically active zone, i.e., a gas-to liquid converting medium, such as an autotrophic production medium, exits on the same side of the catalytically active zone from which it enters, such as a lumen side of a hollow fiber contained in a bioreactor, although the embodiments are not so limited.

In one embodiment, one or more gaseous components, such as a second incompatible gaseous reactant and an autotrophic carbon source, that can enter a second side of the catalytically active zone can exit on the same side of the catalytically active zone from which it enters, such as a shell side of a hollow fiber contained in a bioreactor, although the embodiments are not so limited. In one embodiment, the gaseous components are substantially consumed in the medium in which they are present, leaving little or no gaseous components to exit the bioreactor. As such, in one embodiment, there are no outlet ports or only one outlet port in the bioreactor. In one embodiment, the medium enters and exits on a shell side of the bioreactor and gaseous components enter and exit from a lumen side.

This is in contrast to known monolithic reactors used to conduct chemical reactions which contain parallel channels within a solid matrix. As such, conventional monolithic reactors do not have a continuous "shell side" surrounding the tubes as in the various embodiments described herein, and therefore cannot keep incompatible components separate. The embodiments described herein are also in contrast to the conventional use of hollow fibers for anaerobic synthesis-gas fermentations, which do not involve incompatible gases. Such fermentations maintain the synthesis gas as a continuous phase on only one side of a porous fiber wall and a liquid phase on the other side and therefore do not involve transport of incompatible gaseous reactants to the catalytic component from opposite sides of the fiber wall.

In one embodiment, at least one of the incompatible gaseous reactants is present dispersed as bubbles in a medium comprising a continuous liquid phase and a second incompatible gaseous reactant is present in a medium comprising a continuous gas phase on an opposite side of the catalytically active zone. Molecules of the second incompatible gaseous reactant can reach the catalytic component either by direct contact between the continuous gas phase and the catalytic component at the outer wall of the hollow fiber or by partial dissolution of the second incompatible gaseous reactant in liquid contained within the wall of the hollow fiber and subsequent transport of the dissolved incompatible gaseous reactant to the catalytic component.

In the embodiment shown in FIG. 1, a bioreactor 100 is provided which is adapted or configured to combine gaseous components, such as incompatible gaseous reactants. The bioreactor 100 in FIG. 1 has a shell and tube configuration comprising catalytic component retainers in the form of one or more hollow fibers 102 and a shell side 104 (area outside the one or more hollow fibers 102). Each of the one or more hollow fibers 102 has a wall 124, which, in combination with a catalytic component (203 shown in FIG. 2), located on and/or in the wall 124, form a catalytically active zone 105.

In this embodiment, the shell side 104 has at least one shell side inlet 106 and at least one shell side outlet 108. Similarly, the one or more hollow fibers 102 are in communication with at least one tube-side inlet 110 and at least one tube-side outlet 112.

In one embodiment, each of the one or more hollow fibers 102 is constructed of a substantially cylindrical hollow fiber, having a fiber wall 124 composed of a suitably porous material. In one embodiment, the one or more hollow fibers 102 can be made from porous materials, such as polysulfone, mixed cellulose esters, polyacrylonitrile/polyvinyl chloride (PVC) copolymer and the like.

In one embodiment, the one or more hollow fibers 102 can have a length between about 20 and 10,000 times greater than an inner diameter, and a wall thickness on the same order of magnitude as the inner diameter (e.g., 0.1 mm to 1 cm).

In one embodiment, at least one of the hollow fibers 102 has a fiber wall 124 which includes a "skin" layer with smaller pores (of the designated pore size) and/or a supporting spongy layer with more open pores (larger than the designated pore size). In one embodiment, the skin layer has a pore size too small (e.g., ≤1 micron) for cells of the catalytic component (203, FIG. 2) to pass through, and the spongy layer has a pore size large enough (e.g., ≥2 microns) for cells of the catalytic component (203, FIG. 2) to be embedded therein.

In one embodiment, the pore size rating (i.e., the pore size in the skin layer) is less than 1 micron. In one embodiment, the pore size rating of the porous fiber wall (i.e., membrane) is smaller than the size of the catalytic component, e.g., bacteria (203, FIG. 2).

In one embodiment, the catalytic component retainer is a substantially flat, planar component capable of maintaining incompatible gases on opposite sides of a catalytically active planar zone.

Figure 2:
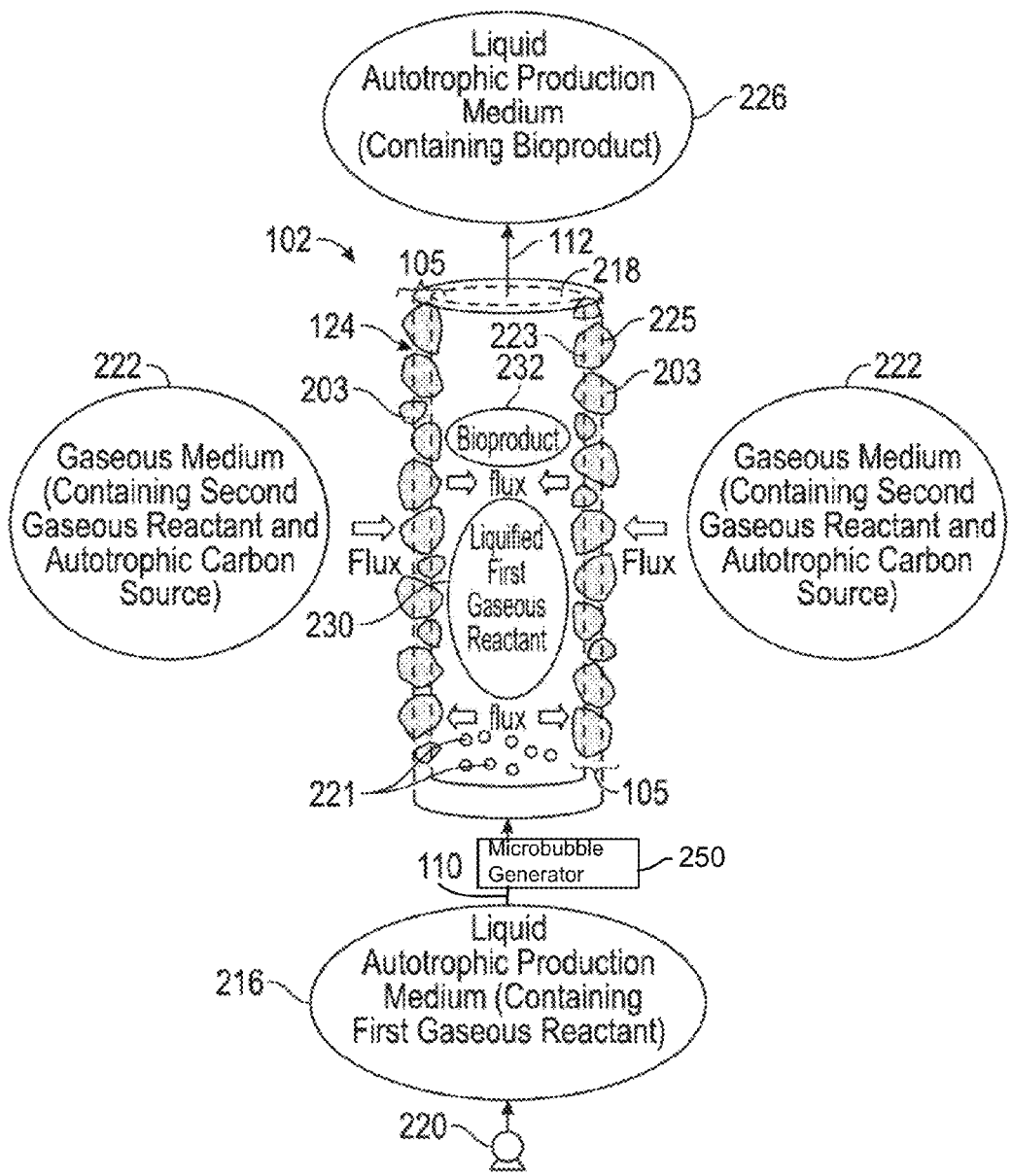
FIG. 2 is a schematic illustration of a catalytically active zone in a bioreactor configured for autotrophic operation according to an embodiment.

Any suitable number of catalytically active zones 105 can be used in a bioreactor 100, depending on the desired output. A detailed view of one of the hollow tubes 102 containing a catalytically active zone 105 is shown in FIG. 2 (Component sizes are not proportional, with, for example, the size of the catalytically active zone and a catalytic component 203 exaggerated for clarity). In the embodiment shown in FIG. 2, a catalytically active zone 105 may be comprised of a catalytic component 203 retained in and/or on the fiber wall 124. (In other embodiments, as described herein, a catalytically active zone additionally or alternatively comprises a liquid medium located on either side of the catalytic component retainer and the catalytic component additionally or alternatively includes a suspended catalytic component suspended in the liquid medium). The catalytic component 203 can be formed from a culture deposited on and/or in the fiber wall 124 and can take on various configurations, have any suitable thickness, or can have a varied thickness. In one embodiment, the catalytic component 203 has a thickness ranging from about 1 to about 50,000 microns.

In the embodiment shown in FIG. 2, the catalytic active zones 105 are substantially the same width as the catalytic component 203 as the cells of the catalytic component 203 are retained on both the inner surface 223 and outer surface 225 of the fiber wall 124, although the embodiments are not so limited. In one embodiment, the cells of the catalytic component 203 are immobilized on and/or within the fiber wall 124, i.e., are effectively immovable under conditions typically encountered in practical bioreactor operation.

In one embodiment, the catalytic component 203 is a biofilm retained on an inner surface 223 of the one or more tubes 102. In one embodiment, the catalytic component 203 is additionally or alternatively a biofilm retained on an outer surface 225 of the one or more tubes 102. In one embodiment, the catalytic component 203 is a biofilm having a thickness suitable for mass transfer of the gaseous components, but not so thick as to produce excessive resistance, which is detrimental to performance of the bioreactor 100.

In the embodiment shown in FIGS. 1 and 2, the tube-side inlet 110 is a liquid inlet into which, for example, a liquid autotrophic production medium (containing a first gas) (hereinafter "autotrophic production medium") 216 is provided to a fiber lumen 218 (i.e., inner hollow area) of the hollow fiber 102, such as with a pump 220. Once inside the hollow fiber 102, the "gas bubbles" 221 within the autotrophic production medium 216 are dissolved therein (at least partially) to form a liquefied first gaseous reactant 230 which can be transported through an inner surface 223 of a porous fiber wall 224 outwardly through to or towards an outer surface 225 of the porous fiber wall 224. As it is transported, the liquefied first gaseous reactant 230 contacts and is consumed by the catalytic component 203 located in the catalytically active zone 105.

In the embodiment shown in FIG. 2, a gaseous medium (consisting of a continuous gas phase containing a second gaseous reactant and an autotrophic carbon source) (hereinafter "gaseous medium") 222 is provided. The second gaseous reactant can comprise an energy source, such as hydrogen gas, and the autotrophic carbon source can be carbon dioxide gas. The gaseous medium 222 can transport inwardly towards the fiber wall 224 where the second reactant and the autotrophic carbon source are consumed by the catalytic component 203 contained therein and/or thereon, in the presence of the second gaseous reactant.

On the molecular scale, the reactants contained in the gaseous medium 222 may additionally be taken up directly by cells of the catalytic component 203 located on an outer surface of the porous fiber wall 224 and/or may dissolve in any autotrophic production medium 216 contained in the porous fiber wall 224. The dissolved reactants from the gaseous medium 222 may then be transported through the porous fiber wall 224 to the cells of the catalytic component 203 which are either entrapped therein and/or bound to an inner surface of the porous fiber wall and/or retained on one side of the catalytic component retainer 224 (i.e., on which the liquid medium is present) where they are consumed to form more catalytic component 105 and/or a bioproduct 232.

In this embodiment, the bioproduct 232 is transported into the fiber lumen 218 containing the autotrophic production medium 216. The bioproduct 232 exits the hollow fiber 102 in the autotrophic production medium 216, which is referred to in FIG. 2 as the "medium (containing a bioproduct)" 226 and exits through the tube-side liquid outlet 112. Although not shown in FIG. 2, the bioproduct additionally or alternatively leave through the shell side outlet 108.

Removal of the bioproduct 232 through the lumen side outlet 112 and/or the shell side outlet 108 allows the bioproduct 232 to be carried away from the catalytically active zone 105, thereby reducing bioproduct inhibition of the catalytic component 203.

Transport of reactants to the catalytically active zone 105 and removal of the bioproduct 232 from the catalytically active zone 105 via diffusion does not involve or require use of a continuous pump, catalytic particles or catalytic particle beds. However, if diffusion alone does not transport the reactants to the catalytically active zone 105 sufficiently fast to avoid reactant depletion within the catalytically active zone 105 and/or remove the bioproduct 232 from the catalytically active zone 105 sufficiently fast to avoid bioproduct inhibition, pressure pulses can be used to induce pulsatile liquid convection between the fiber wall 124 and the fiber lumen 218. Pulsatile flow can be achieved either by cycling the gas pressure on the shell side (104, FIG. 1) or the liquid pressure on lumen side 102.

Although the bioreactors described herein are designed to handle incompatible gaseous reactants, they are contemplated for use with any gaseous components.

As noted above, gaseous components entering the bioreactors described herein are generally solubilized, at least partially, either through dissolution in the liquid phase or direct uptake by the cells of the catalytic component. This includes the incompatible gaseous reactants and any other gaseous components.

Any suitable incompatible gaseous reactants can be used. Such components are generally gases when in pure form under conditions suitable for bioreactor operation (i.e., a pressure between about 0.1 and about 10 atm and temperature between about 10 and about 130° C.), and form incompatible gas phase mixtures with other incompatible gaseous reactants.

In one embodiment, the first incompatible gaseous reactant contains an electron accepting gas, such as oxygen. In one embodiment, the oxygen is present as air (i.e., 21% oxygen) or a gas enriched in oxygen above the concentration found in air. In one embodiment, the oxygen concentration is about 90%, with the remainder being mostly nitrogen.

In one embodiment, a first incompatible gaseous reactant is oxygen and a second incompatible gaseous reactant is methane.

In one embodiment, a first incompatible gaseous reactant is oxygen and a second incompatible gaseous reactant is hydrogen.

In one embodiment, one of the incompatible gaseous reactants contains an energy source (i.e., is an energy rich gaseous reactant), such as hydrogen, methane, ethane, propane, and the like.

In one embodiment, a first gaseous reactant is hydrogen and a second gaseous reactant is carbon monoxide.

Any suitable autotrophic carbon source can be used and can be provided to the shell side 104 (as shown in FIG. 2) and/or the lumen side 102, i.e., on either side of a catalytically active zone. In one embodiment, the carbon source is carbon dioxide. In one embodiment, one of the incompatible gaseous reactants is both an energy source (i.e., energy rich gaseous reactant) and a carbon source. In one embodiment, the carbon source additionally or alternatively enters on the same side as the first gaseous reactant. Although in most embodiments the autotrophic carbon source is used to support bioproduct production after growth of catalytic component 203 has occurred, as described, in one embodiment, the autotrophic carbon source can also be used to support growth of the catalytic component 203 in addition to or instead of a heterotrophic carbon source (discussed below).

In one embodiment, where hydrogen is one of the incompatible gaseous reactants and carbon dioxide is used as the carbon source, the hydrogen concentration can be between about 85 and about 95%, such as at least a 90% and the carbon dioxide concentration can be between about 5 and about 15%, such as at least 15%.

Any suitable medium capable of dissolving an incompatible gaseous component into a compatible reactant liquid can be used in the various embodiments described herein. In one embodiment, the medium is a continuous liquid phase present in an amount sufficient to allow an incompatible gaseous reactant contained therein to dissolve or solubilize, at least partially.

In one embodiment, such as is shown in FIG. 2, the medium is a liquid medium, which, more specifically, is an autotrophic production medium that allows the cells to grow on gaseous carbon and/or energy sources (e.g., $CO_2$ and $H_2$). In embodiments in which one of the incompatible gaseous reactants serves as both a carbon and energy source (e.g., methane), the medium is not an autotrophic but can be any suitable medium (e.g., methanotrophic liquid medium).

In one embodiment, at least one continuous liquid phase has a second phase dispersed therein. In one embodiment there are at least two reacting species which are incompatible while in the gas phase and are kept from mixing to a significant degree while in the gas phase. In one embodiment, the two incompatible reacting species are kept on opposite sides of the catalytically active zone that consumes them both via a chemical reaction.

In one embodiment, the first continuous liquid phase is an aqueous solution and a second (gaseous) phase dispersed in the first phase contains the first gas, such as oxygen, which is kept from mixing significantly in the gas phase with a second (incompatible) gas, such as hydrogen, which is kept on the opposite side of the catalytically active zone 105.

In one embodiment, the second (dispersed) phase is a low solubility liquid contained in a first (continuous) liquid phase, such as a hydrophobic liquid having a low aqueous solubility, and contained in an aqueous solution. In this embodiment, the make-up of the phase present on the opposing side of the catalytically active zone can vary. For example, the third phase can be a continuous gas or liquid phase or may also have another phase dispersed therein. In these embodiments, there is incompatibility between a component in the second (dispersed) phase and a different component in either the third (continuous) phase or a fourth phase dispersed within the third phase. In one embodiment, a four-phase system is provided in which a first (continuous aqueous) phase has a second, gas phase containing oxygen dispersed therein. On the other side of the catalytically active zone, a third (continuous aqueous) phase has a fourth, gas phase containing hydrogen dispersed therein.

Referring again to FIG. 2, although low solubility gaseous components can limit mass transfer rates, use of low solubility gases in the medium containing the first gaseous reactant, such as the autotrophic production medium 216 of FIG. 2, limits flux of the incompatible gaseous reactants. This prevents significant transport of incompatible gaseous reactants through the catalytically active zone 105 and into another gas phase (which can be contained within an autotrophic production medium) on the opposite side of the catalytically active zone 105, thus avoiding or reducing the amount of direct contact between the incompatible gaseous reactants in a gas phase. Specifically, the lower the solubility, the slower the transport of gaseous components from one side of the catalytically active partition to the other. Appropriate pore size and composition of the porous fiber wall 124 also aids in limiting transport of gaseous bubbles. Furthermore, in embodiments in which the gas stream(s) are pumped in a recycle mode through a bioreactor (e.g., 100) and a gas sensor unit, onset of gas mixing can be detected by the gas sensor unit and corrective action (e.g., bioreactor shut-down) can be triggered.

In one embodiment, a mass transport rate, or dissolution rate of the incompatible gaseous reactants into a liquid phase is increased by maintaining the catalytically active zone 105 in contact with one or both incompatible gaseous reactants.

In this way, substantially all of the surface area of the catalytically active zone 105 is in contact with the incompatible gaseous reactants and is available for gas dissolution.

However, when cells of a catalytic component (e.g., 203 in FIG. 2) are present at the surface of the catalytically active zone (e.g., 105 in FIG. 1), the resistance to diffusion for gas dissolved in a gas to liquid converting medium is reduced, and direct gas exchange between a continuous gas phase and the cells is possible without the need for the gaseous component to first dissolve in a gas to liquid converting medium and diffuse through the gas to liquid converting medium and wall (e.g., 124 in FIG. 2) to the cells.

In one embodiment, at least one of the incompatible gaseous reactants is present as bubbles within its medium, as described in FIG. 2 (221). In one embodiment, the bubbles are generated with a bubble generating device in contact with the gas-to-liquid conversion mediums 216, 222. In one embodiment, the bubble generating device is an orifice through which gas is injected when the gas pressure exceeds the surrounding liquid pressure. Once injected into the liquid, the surface tension between the gas and liquid phases causes the gas to form bubbles. The average size of the bubble distribution is controlled by the ratio between hydrodynamic forces, which tend to stretch or break the bubbles, and surface tension, which tends to maintain the bubbles in a spherical shape. Thus, the average bubble size can be adjusted to produce bubbles of a desired size range by controlling the hydrodynamic forces and the surface tension.

In one embodiment, at least some of the first gas bubbles 221 comprise bubbles having a diameter no greater than the inner diameter of the hollow fiber 102. As discussed in more detail below, in one embodiment, at least some of the first gas bubbles 221 can be provided as microbubbles via a microbubble generator 250 (FIG. 2).

In one embodiment, the incompatible gases are soluble. In one embodiment, the incompatible gases are insoluble. In one embodiment, the incompatible gases are sparingly soluble. Gases having low solubility can be either insoluble or sparingly soluble. For example, hydrogen in water at one atmosphere pressure and about 30° C. is reported to have a solubility of 0.00015 g/100 mL and oxygen in water at one atmosphere pressure and about 30° C. is reported to have a solubility of 0.004 g/100 mL. (See www.engineeringtoolbox.com/gases-solubility-water-d_1148.html). According to the definition provided herein, such gases would be considered to be low solubility gases, and, more specifically, insoluble gases.

Any suitable cell or combination of cells can be used together with a carbon source to produce or grow the catalytic component 203 shown in FIGS. 1 and 2 and described above. In one embodiment, any cell (e.g., a microbial cell such as a bacterium) capable of taking up an energy source (such as hydrogen gas), an electron acceptor (such as oxygen) and a heterotrophic carbon source (e.g., sugars, such as fructose) can be used. In one embodiment, any gram-negative bacterium is used. In one embodiment, the catalytic component 203 is engineered for adherence to a catalytic component retainer, such as a fiber wall 124.

In one embodiment, the facultatively autotrophic gram-negative bacterium *Ralstonia eutropha* (*R. eutropha*) is used. In one embodiment, a genetically modified *R. eutropha* is used.

In one embodiment, *R. eutropha* isobutanol product formation rate is increased by continuously removing the IBT from the bioreactor to help minimize growth and metabolism inhibition by product. Additionally, growth of *R. eutro-*

*pha* as biofilms can increase tolerance to IBT, thus reducing inhibition of cell growth and metabolism byproduct.

In one embodiment, the *R. eutropha* is modified according to the methods described in Jingnan Lu, et al., Studies on the production of branched-chain alcohols in engineered *R. eutropha*, App. Micro Biotechnol, published online Aug. 4, 2012. See also Brigham, C. J., et. al., "Engineering *Ralstonia eutropha* for Production of Isobutanol from $CO_2$, $H_2$, and $O_2$," In Lee J. W., editor, Advanced Biofuels and Bioproducts: Springer New York, pp. 1065-1090 (2013) (hereinafter "Brigham"), which is hereby incorporated by reference herein in its entirety.

In one embodiment, *R. eutropha* is engineered to allow for production of IBT from $CO_2$, $H_2$ and $O_2$ at a concentration of greater than 1 g/L up to about 60 g/L or higher, such as up to about 90 g/L, the solubility limit of IBT in water.

In one embodiment, a heterotrophic or autotrophic carbon source is used to grow more cells on and/or in the porous fiber wall after inoculation.

Figure 3:
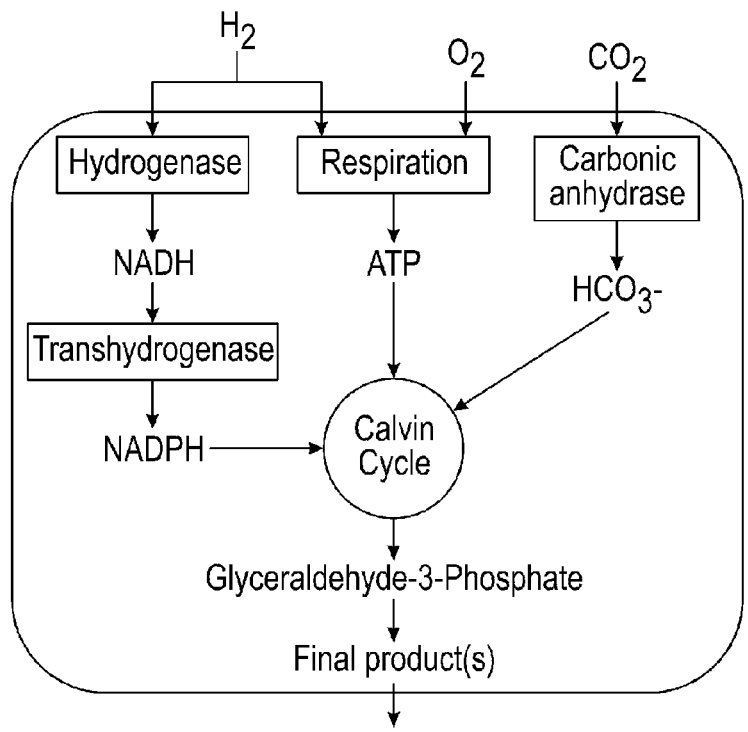
FIG. 3 shows autotrophic metabolism in *Ralstonia eutropha* (hereinafter "*R. eutropha*").

As shown in FIG. 3, the fixation of $CO_2$ into glyceraldehyde-3-phosphate (G3P) via the Calvin Cycle requires both reducing equivalents in the form of NADPH and energy in the form of ATP. The subsequent reduction of G3P to IBT requires reducing equivalents both in the form of NADH and NADPH and energy in the form of ATP. *R. eutropha* possesses at least one hydrogenase that use electrons from $H_2$ to reduce NAD+ to NADH, and at least one other hydrogenase that strips electrons from $H_2$ and passes them though an electron transport chain, which uses $O_2$ as a terminal electron acceptor in the process of respiration to convert ADP to ATP. Additionally, *R. eutropha* contains a transhydrogenase that uses NADH to generate NADPH utilized in $CO_2$ fixation via the Calvin Cycle. *R. eutropha* possesses at least one carbonic anhydrase enzyme, which converts $CO_2$ into bicarbonate ($HCO_3^-$), which serves as the carbon source for the Calvin Cycle. As such, so long as adequate supplies of $H_2$, $CO_2$, and $O_2$ are provided to cells, the SH-transhydrogenase enzyme battery can both deliver the reducing equivalents necessary for both Calvin Cycle $CO_2$ fixation and conversion of pyruvate to IBT. An estimated overall stoichiometry for the gaseous reactants and liquid products associated with the $H_2$-mediated reduction of $CO_2$ to IBT is given below:

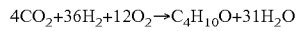

$$4CO_2+36H_2+12O_2 \rightarrow C_4H_{10}O+31H_2O$$

In various embodiments, the bioreactor (e.g., 100, FIG. 1) has a high surface area which enables heat produced within the catalytically active zone 105 (as a result of the chemical reaction) to be removed without an excessive temperature increase, i.e., with a temperature increase less than 10° C. The standard free energy (ΔG°) for production of IBT from $H_2$ and $O_2$ is about 5 MJ/mol isobutanol. Bioreactor variables including the fiber length, wall thickness, and gas and liquid flow rates can be customized for reactions having a variety of reaction rates and ΔG° values, in order to control temperature rise.

Figure 4:
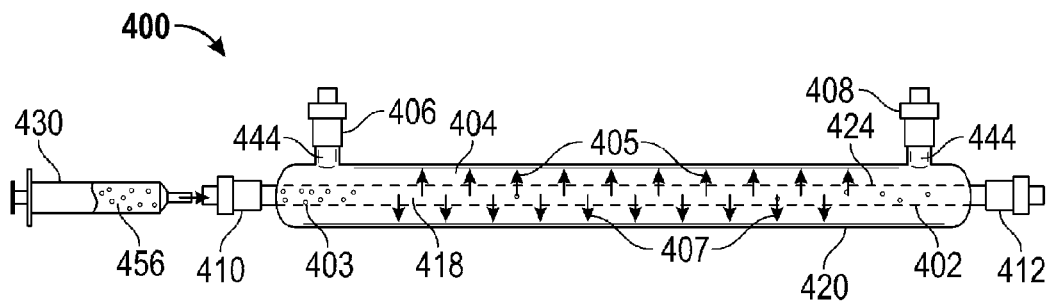
FIG. 4 is a schematic illustration showing "inside-out" inoculation by filtration of a bioreactor according to an embodiment.

The catalytic component (e.g., 203, FIG. 2) can be added in any suitable manner to a fiber wall, such as by a filtration-type inoculation or an incubation-type inoculation. FIG. 4 shows a method for inoculating a single fiber bioreactor 400 in a manner in which a liquid culture comprising a liquid medium 456 containing suspended cells 403 from a liquid culture source 430 (e.g., syringe) is fed into a fiber lumen 418 of a hollow fiber 402 by filtration, thus forcing the liquid medium 490 through the fiber wall 424 from the inside out. Arrows 405 and 407 indicate the direction of culture flow. In this way, the cells 403 are entrapped in larger pores on or within the fiber wall 424. In this embodiment, the hollow fiber 402 is configured such that the fiber lumen (lumen side) 418 is accessible through ports 410 and 412 of a housing 420 and space 404 between the hollow fiber 402 and housing 420 (i.e., shell side) is accessible through ports 406 and 408. In this way, separate fluid streams can be independently pumped through the fiber lumen 418 and through the shell side 404.

In one embodiment, the hollow fiber 402 may have a "skin" layer with pores (smaller than a designated pore size) of the hollow fiber 402) and a supporting spongy layer with more open pores (larger than a designated pore size). As such, when filtering the culture from inside to outside in the manner shown in FIG. 4, if the skin layer is on an inner surface (e.g., 223, FIG. 2) of the fiber wall 424, the cells 403 will be deposited and grow primarily on the inner surface. If the skin layer is on an outer surface (e.g., 225, FIG. 2), the cells 403 will be embedded in open pores within the fiber wall 424. Conversely, when filtering the culture 403 in the opposing direction, i.e., from outside to inside of the hollow tube 402, if the skin layer is on the outer surface (e.g., 225) the cells 403 will end up on the outer surface. If the skin layer is on the inner surface (e.g., 223, FIG. 2), the cells 403 will be embedded in the open pores within the fiber wall 424.

Figure 5:
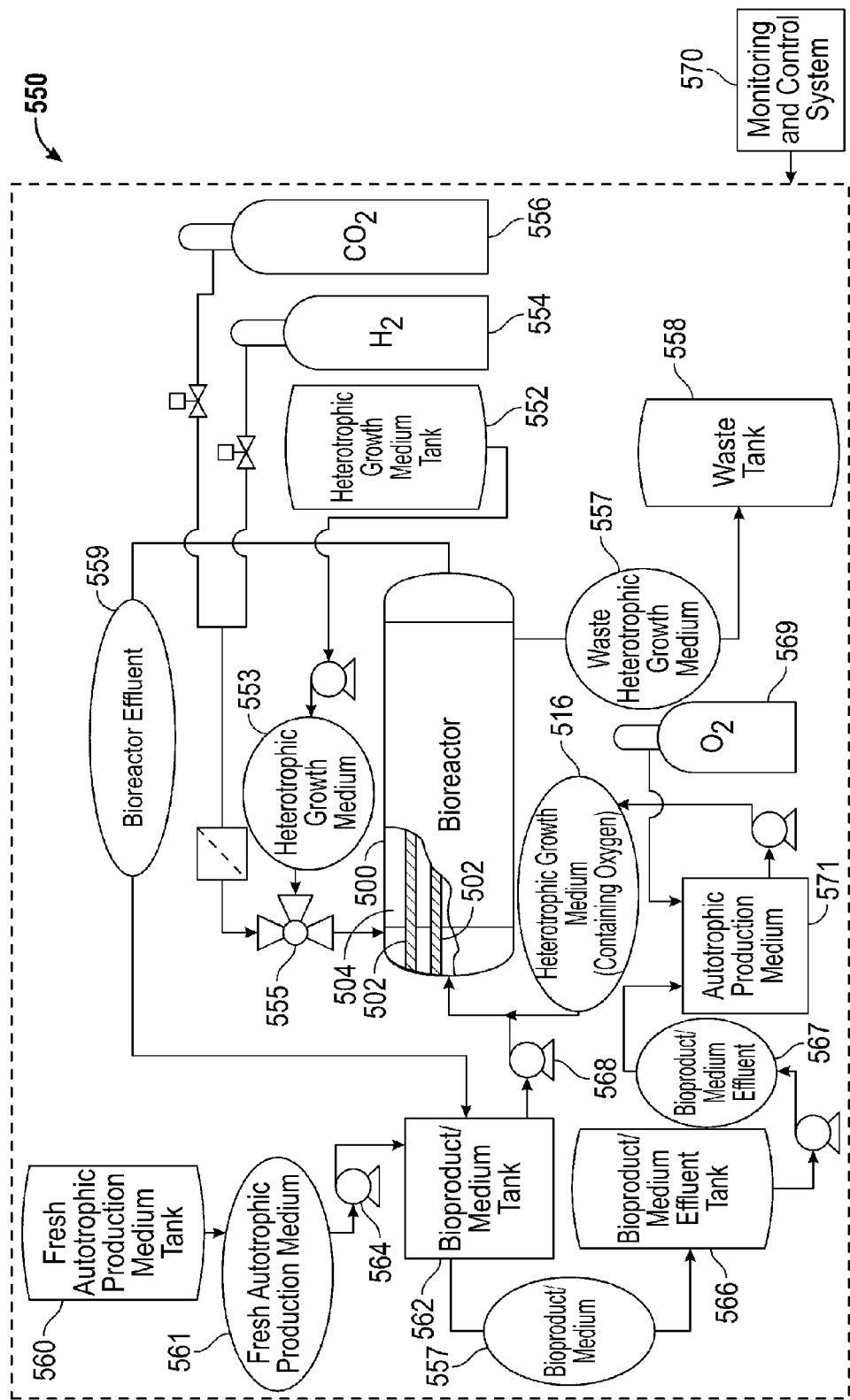
FIG. 5 is a flow diagram of a bioreactor system designed for a two-phase (autotrophic and heterotrophic) operation with cells according to an embodiment.

Referring now to FIG. 5, a system 550 is provided which includes a bioreactor 500 and other equipment in communication with the bioreactor 500. A three-way valve 555 allows a shell side 504 of the bioreactor 500 to be filled with either a heterotrophic growth medium 553 from a heterotrophic growth medium tank 552 for heterotrophic growth or, when autotrophic production of the bioproduct (e.g., IBT) is underway, can be used to provide an energy source (e.g., $H_2$) together with an autotrophic carbon source (e.g., $CO_2$) gas feeds from $H_2$ and $CO_2$ tanks, 554 and 556, respectively.

In one embodiment, during start-up, cells (e.g., *R. eutropha*) are added to the heterotrophic growth medium 553, which is then pumped from the heterotrophic growth medium tank 552 and into the shell side 504 of the bioreactor 500 to inoculate the hollow fibers 502 contained therein and form a catalytic component (not shown) in and/or on the hollow fibers 502 in the form of a biofilm and/or retained cells within and/or on the fiber walls of the hollow fibers 502.

After inoculation, additional heterotrophic growth medium 553 may be pumped through the shell side 504 to support growth of the cells inoculated on hollow fibers 502 in the bioreactor 500 to an appropriate cell density for subsequent bioproduct production.

After inoculation and heterotrophic cell growth is completed, the three-way valve 555 can be used to initiate autotrophic IBT production by terminating flow of the heterotrophic growth medium 553 to the shell side 504 and initiating flow of the gas feed containing an appropriate ratio of $H_2$ and $CO_2$ gases from the $H_2$ and $CO_2$ tanks, respectively. In one embodiment, the flow of gas feed into the shell side 504 of the bioreactor 500 flushes the waste heterotrophic growth medium 557 from the shell side 504 into a waste tank 558.

For both the heterotrophic and autotrophic phases, oxygen from an oxygen tank 569 is provided to an autotrophic production medium tank 571 and, in the embodiment shown in FIG. 5, the autotrophic growth medium (containing oxygen) 516 is provided to the lumen side 502 of the bioreactor 500. Oxygen dissolved in the autotrophic growth medium 516 diffuses to cells (i.e., the catalytic component) (not shown) retained on and/or in the hollow fibers 502 of the bioreactor 500, as discussed above. In this way, the incompatible gaseous reactants ($H_2$ and $O_2$) are simultaneously provided to the cells retained on the hollow fibers 502 without being mixed in the gas phase. In the embodiment shown in FIG. 5, the autotrophic carbon source 556 is provided to the cells from the shell side 504 along with the $H_2$. In one embodiment (not shown), the $CO_2$ is provided from the lumen side 502 along with the $O_2$.

Metabolic activity can be monitored during the autotrophic phase by using any suitable monitoring and control system 570, such as a gas chromatography to monitor gas uptake and bioproduct formation. If the activity drops significantly over time, additional heterotrophic medium 552 can be pumped through the shell side 504 to regenerate catalytic component activity.

In one embodiment, bioproduct concentration can be maintained at a sufficiently low concentration, i.e., bioproduct concentration less than about 20 g/L, to prevent significant bioproduct inhibition of the catalytic component 203. In the embodiment shown in FIG. 5, fresh autotrophic growth medium 561 can be pumped from a fresh autotrophic growth medium tank 560 to a bioproduct/medium tank 562, such as a continuous stirred tank bioreactor (CSTR), by any suitable means, such as with a feed pump 564. The bioproduct/medium tank 562 can be a sterilizable bioreactor capable of controlling pH, temperature, and dissolved $O_2$ (DO) in the medium 557. The bioproduct/medium 557 can overflow into a bioreactor/medium effluent tank 566 which provides bioproduct/medium effluent 567 to the autotrophic production medium tank 571.

A pump 568, such as a peristaltic pump, can be used to recycle the fresh autotrophic production medium 561 from the bioproduct/medium tank 562 through the lumen side 502 of the bioreactor 500 and then back to the bioproduct/medium tank 562 as shown. The flow rate of fresh autotrophic production medium 561 from the fresh autotrophic growth medium tank 560 can be adjusted to control the bioproduct concentration in the bioproduct/medium tank 562 as bioreactor effluent 559, thus reducing the sensitivity of the catalytic component in the bioreactor 500 to bioproduct inhibition.

Individual gas sensors or gas sensors which are part of a gas sensor unit can be used to continuously guard against formation of incompatible gas mixtures, which can result, for example, by $O_2$ leaking into the $H_2$-rich, shell side gas and/or by $H_2$ escaping from the bioreactor or plumbing into the surrounding air. To detect possible oxygen leaks, a gas-phase $O_2$ sensor can continuously monitor the $O_2$ concentration in the shell side gas stream. Hydrogen leaks can be detected using $H_2$ sensors in the vicinity of the bioreactor 500 and/or the compressed $H_2$ cylinder 554. In various embodiments, the gas sensors may have programmable alarms and can be connected to the control system, so the $H_2$ flow can be shut off in response to an alarm. As a precaution against a power outage, a "fail-closed" electronic valve that automatically closes in the absence of power can be used on the $H_2$ stream.

In one embodiment, advanced process control capabilities are used, such as the monitor and control system 570, which can be automated using control software. In one embodiment, gas mass flow meters (not shown) are used on the gas and carbon source feed lines to control the ratio of gaseous component in the shell side 504. The gas ratio can be measured using on-line sensors that simultaneously measure the partial pressures of the $CO_2$ and $O_2$ in the hollow fiber bioreactor effluent gas stream. The $H_2$ concentration in this stream cannot be directly measured with conventional on-line sensors, because these $H_2$ sensors are based on a combustion mechanism based on the presence of $O_2$, but $O_2$ is not expected to be present in this gas stream. However, the $H_2$ partial pressure can be calculated as the difference between the total gas pressure and the measured $CO_2$ partial pressure.

A variety of bubble sizes can be used during operation of any of the bioreactors described herein (e.g., 100, 400, 500). In one embodiment, most or substantially all of the bubbles used during the reaction are substantially the same size. In one embodiment, a combination of bubble sizes ranging from microbubbles (i.e., colloidal gas aphrons), each having a diameter of about 1 to 100 microns (0.001 mm to 0.1 mm) up to larger bubbles, including bubbles having a diameter comparable in size to the inner diameter of an individual hollow fiber (e.g., about 0.01 mm up to 1 mm) are used. Therefore, although conventionally-sized bubbles (e.g., about 1 mm to 10 mm) may be used, in most embodiments, the bubbles are not larger than the inner diameter of each of the hollow fibers for the reasons noted below.

Each bubble size offers particular advantages and disadvantages, so are selected depending on the particular application. Additionally, the size of bubbles can vary during the operation. For example, larger bubbles can provide good radial mixing within the lumen which may be useful in embodiments in which the flow of the liquid phase that carries the bubbles through the lumen.

However, for low solubility gases, the rate of dissolution, from gas into the liquid, is often rate limiting. The rate of dissolution, i.e., the volumetric gas mass transfer rate is directly proportional to the interfacial area between the gas and liquid. Also, if the gaseous and continuous liquid streams are contained within a relatively small region (e.g., the lumen side of an individual hollow fiber), the presence of bubbles that are large relative to the diameter of the fiber can create problems, such as gas slugging, in which a gas bubble occupies substantially the entire cross-section of the fiber lumen.

When a bubble having a diameter considerably larger than the fiber's inner diameter approaches an inlet to a lumen side of a fiber bundle, several outcomes are possible. For example, the bubble may plug the opening of fibers it contacts, resulting in increased liquid flow through adjacent fibers. Additionally or alternatively, the bubble may elongate, so that its cross-section decreases to less than that of the fiber opening. At that point, the bubble may pass through the fiber intact, with a thin, water film separating the gas from the fiber wall. Additionally or alternatively, the bubble may rupture at the fiber opening, causing the gaseous component to pass into the fiber without a liquid film separating the gas from the fiber wall.

Which of these three outcomes occurs depends on the Weber number, which expresses the ratio of hydrodynamic forces that act to deform the bubbles, to surface tension that tends to hold the bubble in a spherical shape. If the surface tension forces dominate, the first outcome would result. If the hydrodynamic forces dominate, either the second or third outcome can result. Moreover, because the viscosity of gases is typically orders of magnitude less than viscosity of water, the third outcome (bubble rupture) can provide a low-resistance flow path for the gas, resulting in continued gas flow from a large bubble until the contents of the bubble were exhausted. The first and third outcomes may thus result in unequal flow through adjacent fibers. Such issues can be avoided by using bubbles which can readily pass through the fiber opening, avoiding not only gas slugging, but also fiber plugging and bubble elongation or rupture.

In one embodiment, most or all of the bubbles are smaller than the inner diameter of the fibers. Because such bubbles do not need to overcome surface tension effects (by stretching or breaking) to get into the fibers, the power for pumping small bubbles into a bundle of hollow fibers (i.e., fiber bundle) which make up the catalytically active partition may be less than the power used to pump larger, conventionally-sized bubbles. In this embodiment (in which most bubbles are smaller than the inner diameter of the fibers) there is likely increased uniformity of gas/liquid dispersion in the hollow fibers.

Other advantages of smaller bubbles include increased mass transfer rate. In one embodiment, the available interfacial area of the bubbles is increased with use of bubbles smaller than the fiber diameter, including microbubbles (i.e., colloidal gas aphrons). Once dissolved into the liquid phase, the gaseous component can be transported, e.g., diffuse, into the catalytic component on or within the porous fiber wall and react within the catalytically active zone. This method may be particularly useful in applications in which one or more additional gaseous component are provided to the catalytic component, or when products are removed because the liquid phase through which the dissolved gaseous component diffuses into the catalytic component can also provide a source of other dissolved reactants, or a sink for products.

In one embodiment, microbubbles are added to the liquid medium before it enters the bioreactor. Since pressure inside a microbubble increases as the microbubble size is reduced, the increase in pressure can result in complete dissolution of the gas, causing the gas bubble to disappear. Thus, in one embodiment, gas microbubbles (e.g., gaseous oxygen microbubbles) are dispersed in a medium entering the lumen of each of the hollow fibers, with liquid containing substantially no gas exiting from the other side. In this embodiment, the gas can become completely consumed as the liquid passes through the fiber. In one embodiment this scheme is used for process control of the system such that gas exiting the bioreactor is an indicator of excessive gas flow rate.

Microbubbles may also provide a more uniform gas/liquid dispersion within each of the hollow fibers than larger bubbles. In one embodiment, the liquid and gas phases are uniformly dispersed within the hollow fibers, as indicated by a roughly equal proportion of gas and liquid in each fiber of the matrix, and avoidance of long stretches of fiber containing only liquid alternating with long stretches of fiber containing only gas. A continuous gas phase in contact with the outside of the fiber provides rapid mass transfer from the outside in, and the small bubbles in the fibers provide good mass transfer from the inside out.

In one embodiment, the method used to make small bubbles provides gas/liquid dispersions having a desired ratio of gas to liquid and bubble distribution. In one embodiment, the gas/liquid dispersion has an average diameter smaller than an inner diameter of the hollow fiber. When the inner diameter of the hollow fiber is large as compared to the bubble size, the bubbles are not be significantly affected by the aforementioned surface-tension based effects (bubble exclusion, stretching, or rupture) at the openings, thereby enabling the good gas distribution initially present to continue into the bundle. This hydrodynamic advantage is in contrast to conventional approaches which use hollow-fiber bioreactors for synthesis gas fermentations, which do not involve two incompatible gases. Under such circumstances bubbles are not used because a single phase (e.g., gas) can be maintained on one side of the catalytic barrier, and another single phase (e.g., liquid) can be maintained on the other side.

In one embodiment, the method used to make microbubbles generates a relatively wide size distribution. In one embodiment, surfactants are not added to the liquid. As a result, the average diameter of microbubble dispersions can increase with time for a number of reasons, such as by collision of smaller bubbles and resulting coalescence into larger bubbles, and/or Ostwald ripening. In Ostwald ripening, gas diffuses from smaller having higher internal pressure to larger bubbles having lower internal pressure. As a result, smaller bubbles get smaller and then disappear altogether, while larger bubbles grow in size. Therefore, in one embodiment, the initial bubble size distribution is sufficiently small, such that most of the bubbles have diameters smaller than the inner diameter of the fibers and can enter the fibers with minimal interaction with the fiber opening. Thereafter, the geometry of the fiber keeps the small bubbles segregated and thereby controls coalescence due to bubble collisions.

In one embodiment, the smaller bubbles provide high mass transfer driving force and rate of gas dissolution into the water, while coalescence and Ostwald ripening provide a sufficient number of bubbles similar in diameter to the inner diameter of the fiber. In this way, rapid radial mixing is provided to cause gas molecules to dissolve in the water and be transported to the fiber wall by diffusion or convection where they can be consumed by the catalytic component. As such, sufficient coalescence can occur to enhance radial mass transfer rate, but not so much as to require the bubbles to be broken up more than once.

This is in contrast to conventional bioreactor configurations in which ongoing collisions result in coalescence, which reduces the interfacial area between the gas and liquids and thereby reduces the mass transfer rate, and is therefore a major problem. As such, conventional systems require use of large impeller motors that rely on impeller shear to continuously break up the large bubbles formed by coalescence into smaller bubbles, in order to transfer gas more efficiently. However, such impellers consume large amounts of energy, resulting in high power costs.

Because microbubbles are about three orders of magnitude smaller than conventional bubbles and can be produced in an energy-efficient manner, microbubbles offer outstanding potential for cost-effective mass transport enhancement.

Microbubbles can be formed by creating high shear rates in the vicinity of a gas-liquid interface. The presence of a surfactant can stabilize the microbubbles by imparting an electric double layer, which reduces bubble coalescence by electrical repulsion of adjacent bubbles. The resulting microbubble dispersion can have a void volume exceeding 60% and is stable enough to be pumped without significant coalescence. Thus, microbubble foams can be produced energy-efficiently in a small vessel and pumped into a much larger bioreactor.

In addition to bubble size reduction, another strategy to achieve rapid, energy-efficient gas mass transport in bioreactors is to provide direct contact between the cells and a continuous gas phase. Under these conditions, the gas flow rate may be set low enough to achieve a high conversion without a substantial loss in $k_L a$.

Oxygen microbubbles can be formed from the autotrophic medium and a low concentration of a non-toxic surfactant, such as TWEEN 20, using a spinning-disk microbubble generator such as a generator used in continuous synthesis-gas fermentations. A concentrated microbubble dispersion can be metered into the autotrophic medium stream using a pump, such as a peristaltic pump, with the flow rate adjusted by the control system to maintain a target dissolved oxygen (DO) concentration in the bioreactor's effluent stream (measured using a dissolved oxygen probe). Make-up liquid to replace that lost in the microbubble dispersion can come from the bioreactor/medium effluent tank 566 shown in FIG. 5.

Alternatively, microbubbles can be generated without added surfactant using a microbubble generator that works by achieving highly turbulent flow and a high Weber number for gas-liquid flow. The hydrodynamic forces resulting under such conditions break up the gas phase into bubbles, whose diameter decreases as the liquid flow rate increases. The use of an appropriate combination of liquid flow rate (e.g. aqueous superficial velocity of about 20 ft/sec (6.1 msec) through a tube having an inner diameter of about 5 mm) and gas volume fraction (e.g., about 3%) can generate a microbubble dispersion. Once formed, these microbubbles can be delivered into the openings of the hollow fibers. Once inside the fiber lumen, the rate of coalescence through collisions between microbubbles would be greatly reduced compared to a microbubble dispersion in free solution, because the walls of the hollow fibers would provide barriers preventing collisions between microbubbles in adjacent fibers.

Collisions between microbubbles in close proximity within a fiber can result in minor coalescence. However, once the bubble diameter approached the inner diameter of the lumen, the bubbles would pass through the fiber separated by discrete segments of liquid, which would serve as additional barriers to prevent further collisions between bubbles. In this way, operation can be achieved without the need to add surfactants to stabilize the microbubbles against coalescence. Moreover, once the microbubbles are added to the fibers, the limited coalescence that can occur between adjacent microbubbles that are much smaller than the lumen's diameter can result in bubbles having a diameter similar to that of the lumen. Such bubbles can benefit performance by enhancing radial mass transfer. Thus, this embodiment naturally achieves an amount of coalescence needed to increase radial mass transfer while avoiding formation of bubbles larger than the inner diameter of the lumen.

The bioreactors described herein can be scaled up for commercial applications in a variety of ways, such as by increasing the length of each hollow fiber. However, when fiber length is increased, both the pressure drop and the bioproduct concentration in the lumen increase. Additionally or alternatively, more fibers can be added to the bioreactor bundle in parallel. However, this approach may ultimately lead to pressure drop on the shell side during flow of the heterotrophic liquid feed across the fiber bundle. Alternatively or additionally, multiple bioreactor modules can be operated in parallel and/or the interfacial area per unit reactor volume can be increased. A mathematical model of the bioreactor can be developed to facilitate control-system tuning, bioreactor optimization, and scale-up. The model can describe mass transport of multiple reactants and products, reaction kinetics, and heat transfer.

In one embodiment, the total reactor volume and/or power consumption of scaled up units are lower than that required for a stirred-tank reactor. In one embodiment, the bioreactor is a hollow-fiber bioreactor (HFR) having a large interfacial area per unit volume (e.g., at least about 1 $mm^2$ surface area/$mm^3$ total reactor volume), enabling rapid interphase mass transfer without the high energy requirements of other systems, such as stirred tanks. As a result, the volume of the bioreactor is expected to be less than conventional bioreactor configurations. In one embodiment, the structure of the hollow fiber can be customized for specific applications. For example, in one embodiment, an anisotropic fiber having a thin (i.e., less than about 0.1 mm) "skin" located at the inner boundary of the fiber and a macroporous matrix on the shell side can be used. Such a skin can prevent cells in the catalytic component from escaping into the fiber lumen, while the porous fiber wall can facilitate inoculation, rapid colonization and formation of a catalytic component having a high cell density, sufficiently high such that the reactor's volumetric reaction rate is not limited by the cell density.

In one embodiment, an in-situ IBT recovery system for the bioreactor is used to reduce inhibition, such as *R. eutropha* inhibition, by IBT. Such systems include, but are not limited to, adsorption onto solid packing, gas stripping, and pervaporation. In adsorption, the fermentation liquid can be contacted with a solid resin that selectively adsorbs the product, typically using a packed column. After the resin is fully loaded with the product, the product is desorbed, regenerating the resin for another recovery cycle. In stripping, a gas stream can be bubbled through the fermentation broth, and volatile fermentation products can be partitioned into the gas with a selectivity that is determined by their relative vapor pressures. In pervaporation, a vacuum can be applied across a semi-permeable membrane, resulting in transport of volatile components through the membrane. Because the product typically has a much lower concentration than water in the fermentation broth, the pervaporation membrane is expected to exhibit high selectivity for the product.

In one embodiment, a hollow fiber bioreactor is provided having one or more hollow fibers within which cells can be grown, a stirred-tank bioreactor capable of programmable control of temperature, pH, dissolved oxygen, and foam, a product recovery unit consisting of packed columns, and a process monitoring and control system to capable of measuring concentrations of key gaseous components and implementing control loops to control the flow rates of gaseous components via mass flow controllers and liquids via variable-speed peristaltic pumps with remote-control capability.

Figure 6:
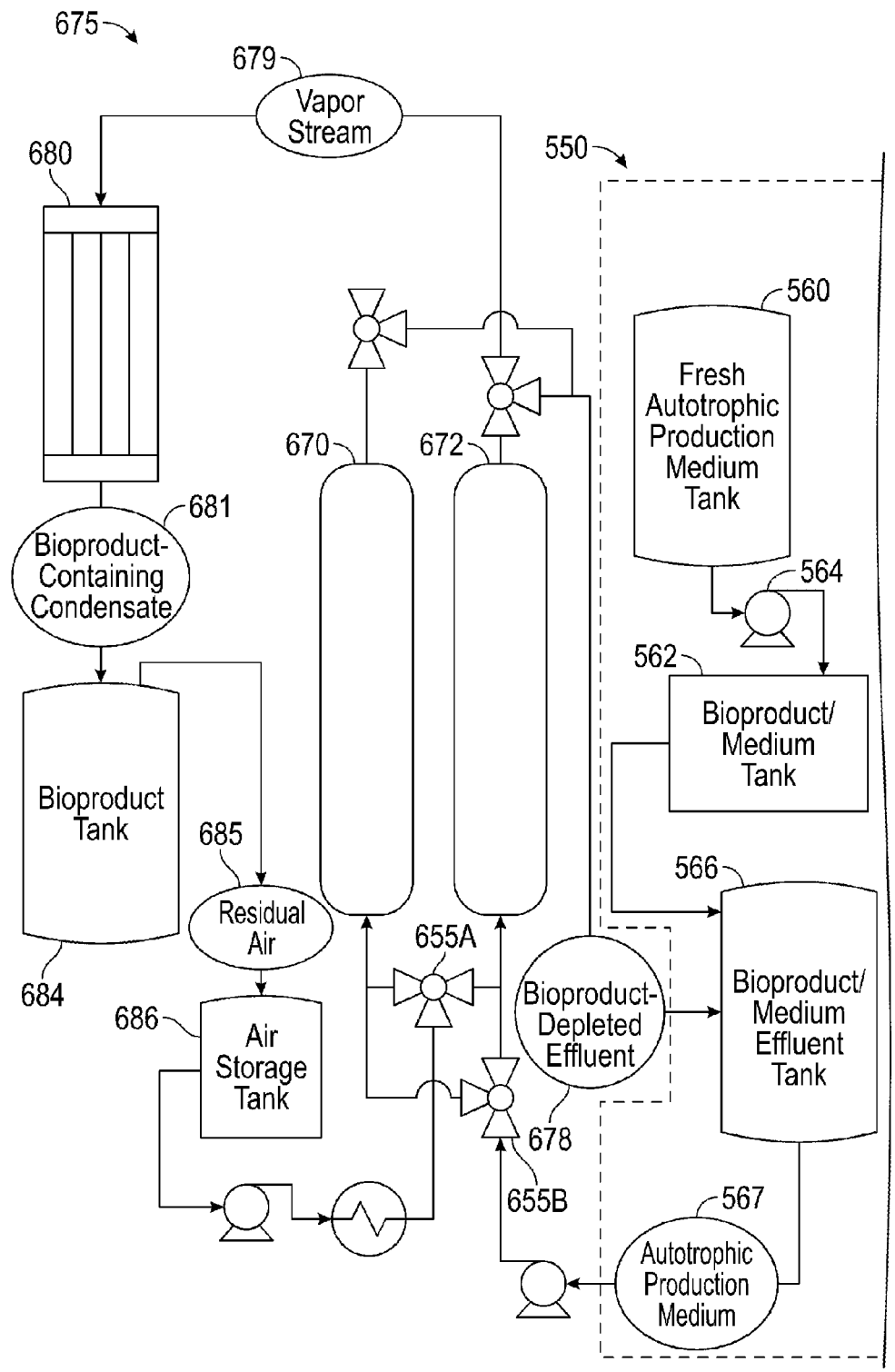
FIG. 6 is a flow diagram of an in situ biofuel recovery system using the bioreactor system of FIG. 5 according to an embodiment.

FIG. 6 shows one embodiment for the separation and recovery of a bioproduct produced as described in FIG. 5. The bioproduct recovery system 675 is via adsorption and includes components integrated with bioreactor system components. (Only components in the autotrophic medium tank 560, the bioproduct/medium tank 562 and bioreactor/medium effluent tank 566 from FIG. 5 are shown for simplicity).

The bioproduct recovery system 675 shown in the embodiment in FIG. 6 includes two columns 670 and 672. In this way, the bioproduct can be adsorbed onto one column while being simultaneously desorbed from the other. Therefore, even though each column 670, 672 can be operated in a batch mode, a continuous operation of the bioreactor system 500 is possible. Both columns, 670 and 672, can be packed with a bioproduct-selective resin (e.g., silicalite for embodiments in which the bioproducts is IBT).

In this embodiment, during the adsorption step, the bioproduct/medium effluent 567 from the bioreactor/medium effluent tank 566, which can be a liquid product, such as an aqueous product, can be pumped through column 670 or column 672 and the bioproduct-depleted effluent 678 can be returned to the bioreactor/medium effluent tank 566. Once a particular column, 670 or 672, is fully loaded with the bioproduct, heated compressed air can be passed through the column to desorb and vaporize the bioproduct to produce a vapor stream 679 containing the bioproduct. The vapor stream 679 can be passed through a condenser 680 and a bioproduct-containing condensate 681 can be collected in a bioproduct tank 684. Residual air 685 can be provided to an air surge tank 686 for temporary storage before reuse. Three-way valves 655A and 655 B can be operated automatically by a control system (e.g., similar to the monitoring and control system 570 of FIG. 5) so that each column 670 and 672 is alternately loaded and then regenerated.

With slight modifications, the same bioproduct recovery system can be used for bioproduct recovery by gas stripping. However, because gas-stripping columns can be operated continuously, only one column may be needed. In this embodiment, the bioproduct/medium effluent 567 may be pumped into a stripping column (670 or 672) that is operated in countercurrent, trickle-bed mode. Air from the air storage tank 686 can be pumped in a recycle loop up through the stripping column (670 or 672) through the condenser 680, and then back to the air storage tank 686. The flow rates of the bioproduct/medium from tank 562 and air from the bioproduct tank 684 can be optimized based on well-established chemical engineering principles.

In certain embodiments a catalytic component has reversible enzyme-catalyzed reactions that allow it to consume the desired product if the dissolved gaseous energy source (e.g., $H_2$) levels are too low. In other embodiments a catalytic component does not have reversible enzyme-catalyzed reactions that allow it to consume the desired product, offering the potential for higher product yields from the reactor.

In certain embodiments, the flow rate of gas leaving the continuous gas phase may approach zero, in order to minimize loss of unreacted gas from the continuous gas phase. (See, for example, the "dead-end" operational mode described in Example 13). In such embodiments, the flow rate of the gaseous reactant(s) into the continuous gas phase is selected so as to maintain a desired gas pressure within the continuous gas phase. In one embodiment, the $H_2$ gas is provided at a pressure of about 10 to about 20 psig. In one embodiment, a pressure of at least, or no more than, 15 psig is used.

In certain embodiments (such as the "dead-end" operational mode described in Example 13), insufficient flow of gas out of the continuous gas phase may result in undesirable accumulation of gases within the continuous gas phase. In one embodiment, the dead-end operational mode allows accumulation of unreactive $N_2$ gas in the continuous gas phase, thereby diluting the reactant gas (such as $H_2$) and reducing the mass transfer rate. In one embodiment, the dead-end operational mode allows accumulation of one reactant gas (such as $O_2$) in the continuous gas phase containing a second, incompatible reactant gas (such as $H_2$), potentially creating an incompatible gas mixture.

To avoid undesirable accumulation of unwanted gas within the continuous gas phase, gas flow out of the continuous gas phase may be increased, either continuously or for a short period of time (e.g., on the order of seconds or minutes or hours, depending on bioreactor configuration) or for designated intervals (also variable, such as on the order of minutes, depending on reactor configuration) to flush out any unwanted gas (such as $N_2$ and/or $O_2$) that may otherwise accumulate in the continuous gas phase and dilute a reactant gas and/or create an incompatible gas mixture In one embodiment, a near-zero flow rate operation reduces the amount of unreacted $H_2$ gas leaving the shell and the amount of IBT vapor lost from the bioreactor in the shell-side effluent gas stream.

Embodiments will be further described by reference to the following examples, which are offered to further illustrate the various embodiments. It should be understood, however, that many variations and modifications may be made while remaining within the scope of the embodiments described.

EXAMPLE 1

Control System

A movable Opto 22 control system (Temecula, Calif.) comprising two grounded electrical boxes containing Opto 22 power supplies (SNAP-PS5), controllers (SNAP-PAC-R1) and racks (SNAP-PAC-RCK16), and I/O modules (SNAP-AOV-25, SNAP-AIMA-4) was used.

The Opto 22 control system measured key variables and controlled various devices, thus providing for continuous operation. A variety of accessory sensors, actuators and electronics were also installed, including gas-phase sensors for $O_2$, $H_2$ and $CO_2$, mass flow controllers, computer-controlled peristaltic pumps, and solenoid valves for emergency shut of gas flow. The ability of the Opto 22 control system to automatically communicate with the sensors, gas chromatograph, a Sartorius BIOSTAT® B plus Fermentor with twin 1-L bioreactors (Sartorius Stedim Biotech North America Inc., Bohemia, N.Y.) (hereinafter "Sartorius fermentor") and effect process control via the actuators was confirmed.

The Sartorius fermentor was equipped with multiple control loops to control various parameters, such as temperature, rpm, oxygen concentration, pH, and in each vessel was used in the multi-fiber bioreactor. A generic glass container (250 ml) was used as a liquid medium reservoir in the single fiber bioreactor. The flow rates of gases were also controlled via mass flow controllers and the flow rate of liquids were controlled via variable-speed peristaltic pumps.

The Sartorius fermentor was connected to a desktop computer and was remotely controlled using BioPAT® MFCS/win supervisory bioprocess control software (Sartorius Stedim North America Inc., Bohemia, N.Y.). Data communication was established between the Sartorius fermentor software and Opto22 system using Cogent DataHub® (Cogent Real-Time Systems, Inc. Georgetown, Ontario, Canada).

Establishment of Communication Protocols

The Sartorius fermentor controlled the pH, temperature, and dissolved $O_2$ concentration in the liquid feed delivered to the hollow fiber bioreactor. The gas chromatograph monitored the IBT concentration in the recirculating liquid. Two-way information flow between these components and the Opto 22 system was used to achieve the process control objectives. Cogent DataHub software was used to mediate information exchange between the OPC servers of the Opto 22 system and the Sartorius Fermentor. The ability of the Opto 22 controller to change control set points for pH and stirring speed of the Sartorius Fermentor was confirmed. Transmission of IBT concentration data from the gas chromatograph to the Opto 22 system was achieved via an ASCII formatted spreadsheet. MATLAB was used as intermediate tool for exporting the spreadsheet, which was periodically stored in the desktop computer running the Opto 22 software Validation of Control and Safety System for the Multi-fiber Bioreactor Multiple levels of safety precautions were implemented. The experimental setup, including all gas cylinders, valves, and bioreactor components, were assembled in a walk-in fume hood. Multiple gas-phase sensors were installed to detect $H_2$ leaks or accidental mixing of $O_2$ into the $H_2$ gas stream. A solenoid shut-off mechanism with an alarm was integrated with the Opto 22 system to instantly shut off $H_2$ flow from the tank in the event of a power failure or in other situations as needed. The mass flow controllers and solenoid valves used were explosion proof and designed specifically for combustible gases. Additionally, the gas line included a check valve that only allowed only one-way flow.

EXAMPLE 2

Preparation of Minimal Growth Medium

All chemicals were obtained from J.T. Baker (Avantor Performance Materials, Center Valley, Pa.) at A.C.S Grade.

Stock solutions containing the following components were prepared in separate containers: 3.9 g/100 mL anhydrous magnesium sulfate; 0.62 g/100 mL anhydrous calcium chloride; a 1000 times concentrated trace salts solution in 0.1 N HCl (i.e., 48 mg/100 mL cupric sulfate $5H_2O$, 240 mg zinc sulfate $7H_2O$, 240 mg manganese sulfate $1H_2O$, 1500 mg Ferrous sulfate $7H_2O$); 80% weight/volume (w/v) fructose solution and 10% w/v ammonium chloride.

In order to produce about 1 L of medium, 33.5 mL 1M sodium phosphate (monobasic), 64.5 mL 0.5 M sodium phosphate (dibasic), 5.2 mL 0.5 M potassium sulfate and 1 mL 1 N sodium hydroxide was added to about 750 mL of distilled water. Additional water was added to produce 1 L.

As is known in the art, the two phosphate salts served to buffer the pH during fermentation; fructose was the carbon and energy source; ammonium chloride was the nitrogen source; and the trace salts were required for the enzymes in the bacteria to ammonium chloride.

The resulting mixture was autoclaved for 20 min at 121° C. in an AMSCO 2021 Gravity sterilizer (STERIS Corporation, Mentor, Ohio) and then cooled to about 50° C. Thereafter approximately 10 mL/L magnesium sulfate, 10 mL/L calcium chloride and 1 mL/L trace salts solution were added to the resulting mixture.

As is known in the art, a medium that is rich with a carbon source but poor in a nitrogen source promotes formation of carbon-rich products by *Ralstonia eutropha* (*R. eutropha*) while suppressing microbial cell growth. A medium rich in both carbon and nitrogen sources promotes cell growth, such as microbial cell growth.

For media used to suppress growth of *R. eutropha* while promoting formation of products such as polyhydroxyalkanoates (PHA) or IBT, 25 mL/L 80% w/v fructose was added to achieve a final fructose concentration of 2% w/v. One (1) mL/L 10% w/v ammonium chloride was also added to achieve a final concentration of 0.01% w/v ammonium chloride.

For media intended to promote growth of *R. eutropha*, 25 mL/L 80% w/v fructose, and ten (10) mL/L 10% w/v ammonium chloride were added.

EXAMPLE 3

Filtration-Type Inoculation of *R. eutropha* Using Hollow Fibers

A minimal growth medium was prepared as described in Example 2.

Filtration was used to inoculate a single fiber bioreactor comparable to the bioreactor 400 shown in FIG. 4 with *R. eutropha* cells (OD600=5.7) (strain Re2061). This bioreactor was made in-house according to the method described in Reiken, S. R., and D. M. Briedis. 1990, The use of a single-fiber bioreactor for the enzymatic removal of amino acids from solutions. Biotechnology and Bioengineering 35:260-267.

The bioreactor was comprised of a single polysulfone hollow fiber (e.g., 104) (Product No. CLF2E110, GE Healthcare, Piscataway, N.J.) with porous walls (e.g., 424) and an overall outer diameter of 1 mm. The fiber was immobilized in a housing, which comprised a 21.5 cm long glass tube having an 8 mm outer diameter, both with an epoxy glue and via short perpendicular glass tubes 444 (5 mm in outer diameter, 14 mm in length) attached near each end of the glass tube. As such, a shell side (e.g., 404) of the bioreactor 400 was created between the outside of the hollow fiber (402) and the inside of the housing (e.g., 420, FIG. 4).

To inoculate the hollow fiber, approximately 5 ml of the *R. eutropha* culture grown in a tryptic soy broth medium (Becton Dickinson, Franklin Lakes, N.J.) was added via a syringe (i.e., under pressure) into the shell side 404 of the bioreactor (e.g., 400). In contrast to the "inside to outside" approach shown in FIG. 4, the inoculation in this example was done "outside to inside." The pressure imparted by the syringe was sufficiently high to allow the liquid medium to pass through the porous wall (e.g., 424, FIG. 4) of the hollow fiber (e.g., 402, FIG. 4) into the fiber lumen and then exit the fiber through the fiber lumen (e.g., 418, FIG. 4). Because all of the cells in the culture were too large (>1 μm) to pass through the pores of the fiber wall (424), they were retained either on an outer surface (e.g., 225, FIG. 2) or within pores of the fiber wall (124, 424). As such, the final location of the *R. eutropha* cells depended on the pore size distribution within the fiber wall, which was nominally 0.2 μm for the single fiber bioreactor (See definition section with respect to variances in pore sizes). Substantially all the *R. eutropha* cells were retained in the fiber wall. Most of the liquid medium that passed through the fiber wall was collected from lumen-side ports. In this testing, the volume of liquid that did not pass through the fiber wall was minimal and not measured.

Since the focus of this experiment was to characterize microbial cell retention in the fiber wall following inoculation, no incubation was performed. As such, the shell side 404 and lumen side 402 of the hollow fiber 424 were rinsed with about 5 ml of 50 mM Tris-HCl buffer (pH 7.5) to remove any loosely attached cells. The fibers were then sectioned into about 2-10 mm lengths and imaged using a JEOL 6400 scanning electron microscope (SEM).

Figure 7A:
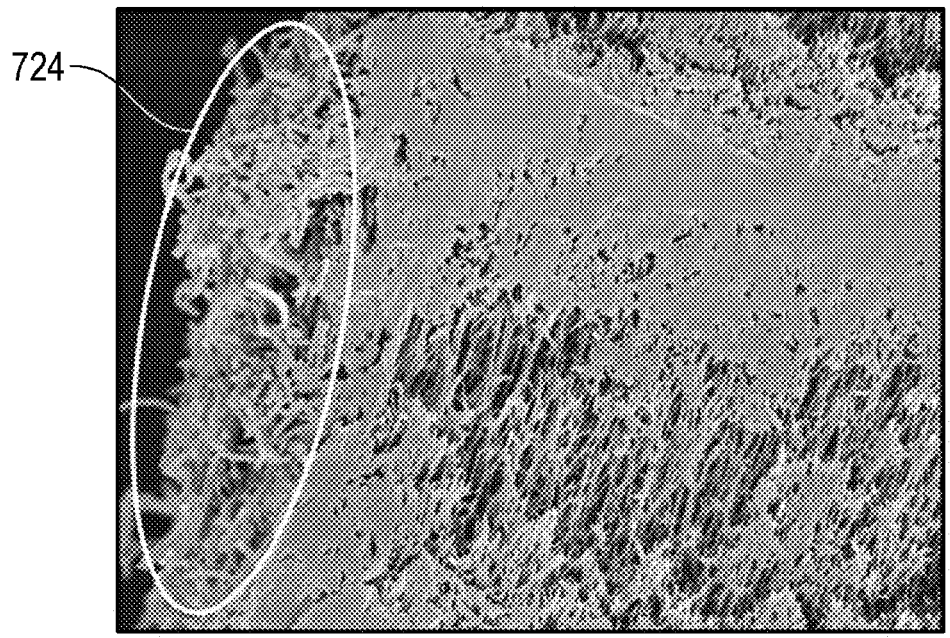
FIGS. 7A and 7B are Scanning Electron Microscopic (SEM) images of a cross sectional area of a polysulfone hollow fiber inoculated using filtration according to an embodiment.
Figure 7B:
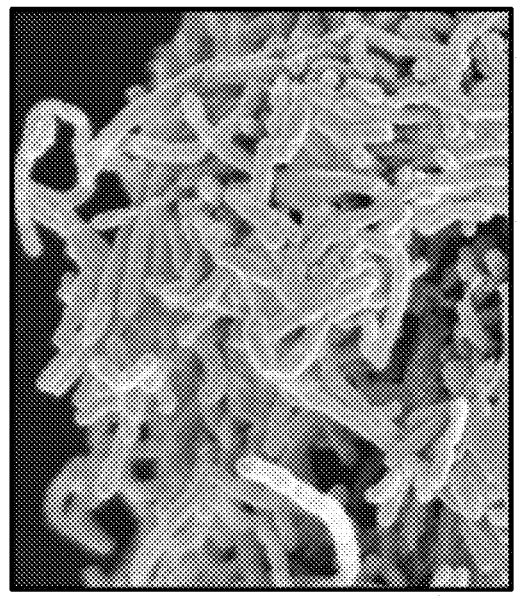

FIGS. 7A and 7B are SEM images of the cross-sectional area of one of the polysulfone hollow fibers inoculated as described above. As shown in FIG. 7A, this method resulted in patches of biofilm that did not penetrate deeply into the spongy layer (porous wall) of the hollow fiber. The circled area 724 in FIG. 7A shows *R. eutropha* biofilm developing on the membrane surface. FIG. 7B shows a patch of biofilm from the circled region at a higher magnification.

These results indicate the pore size of the polysulfone fibers was too small to allow substantial entry of *R. eutropha* cells into the pores, likely resulting in poor microbial cell retention in or on the polysulfone fiber wall. There was no assessment made in this testing as to the merits of inoculating by filtration (under pressure) as compared to incubation (not under pressure). See Example 5 for comparison testing in this regard.

EXAMPLE 4

Verifying Use of R. eutropha with Cellulose Ester Hollow Fibers

Minimal growth medium was prepared as described in Example 2.

Mixed cellulose ester hollow fibers (Spectrum Laboratories, Inc. Rancho Dominguez, Calif.) were cut to approximately 1 cm in length and submerged and incubated in 2 mL of a R. eutropha culture (Re2061) in the minimal medium containing 2% fructose (Sigma-Aldrich, St. Louis, Mo.) in two test tubes.

The test tubes were incubated at 30° C. (Gyrotory Water Bath Shaker, New Brunswick Scientific Co, Inc. Edison, N.J.) for eight days. The medium was changed daily to ensure continued culture growth. The fibers were them sectioned into 2 to 10 mm lengths and imaged as described above.

Figures 8A, 8B:
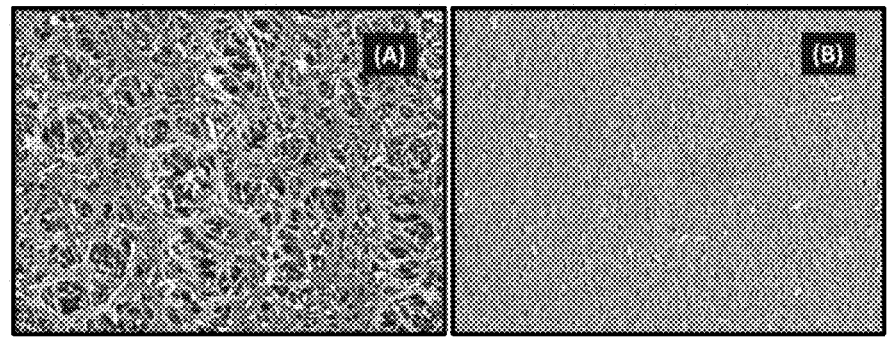
FIGS. 8A and 8B are SEM images of the interior and exterior surfaces, respectively, of a mixed cellulose ester hollow fiber eight days after being inoculated using incubation according to an embodiment.

SEM images of the mixed cellulose ester fibers inoculated by incubation shown in FIGS. 8A and 8B indicated that the inner surface (223, FIG. 2) of the mixed cellulose fibers has a larger pore size (likely greater than 0.2 μm with pores of varying sizes up to 10 μm) as compared to the pore size (0.2 μm) of the outer surface (e.g., 225, FIG. 2).

As such, it was apparent that a microbe such as R. eutropha was properly sized to enter the pores, facilitating retention on or within a mixed cellulose ester fiber.

EXAMPLE 5

Mixed Cellulose Ester Single Fiber Bioreactor

A mixed cellulose ester single fiber bioreactor using fibers from the same source in Example 4 was constructed using the same design as the polysulfone single-fiber bioreactor described in Example 3. The fiber was inoculated with 3 mL of R. eutropha culture at OD600 of 4.8 using the "inside to outside" approach shown in FIG. 4.

Figures 9A, 9B:
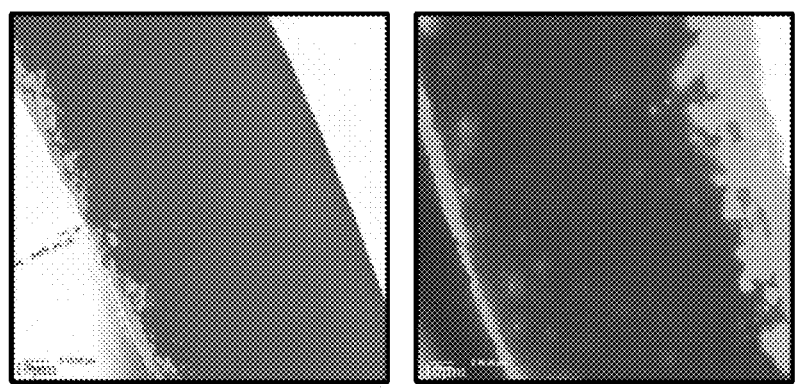
FIGS. 9A and 9B are confocal microscopy images showing a cross section of mixed cellulose ester hollow fiber segments taken from upstream (FIG. 9A) and downstream (FIG. 9B) regions of the hollow fiber according to an embodiment.

The bioreactor was placed in the incubator (Gyrotory Water Bath Shaker, New Brunswick Scientific Co, Inc. Edison, N.J.) at about 30° C. for 18 days with the same minimal medium containing 2% fructose described above, which was circulated with a pump (Masterflex® peristaltic pump, model No. 7553-60, Cole-Parmer, Vernon Hills, Ill.) in the shell side. Air at a rate of 0.05 ml/min was provided to the fiber lumen at a pressure of approximately 5 $lb_f/in^2$ (0.34 atm). At the end of the incubation, the hollow fiber was sectioned for confocal microscopy and fluorescamine protein assay described in Udenfriend, S., S. Stein, P. Böohlen, W. Dairman, W. Leimgruber, and M. Weigele. 1972. Fluorescamine: A Reagent for Assay of Amino Acids, Peptides, Proteins, and Primary Amines in the Picomole Range. Science 178:871-872, hereby incorporated by reference herein in its entirety FIGS. 9A and 9B show the confocal microscopy images of a cross section of hollow fiber segments taken from upstream (FIG. 9A) and downstream (FIG. 9B) of the liquid medium. The cells were stained with green fluorescent dye Invitrogen® SYTO9 (Life Technologies Corporation, Grand Island, N.Y.). These images revealed an approximately 20 μm thick microbial cell layer) at the inner wall of the spongy layer, although much of the spongy layer was devoid of R. eutropha cells, likely due to the relatively small average pore size (0.2 μm) of the fiber walls.

The small pore size within the porous fiber wall was confirmed by tunneling electron microscopy (TEM) images.

Figures 10A, 10B:
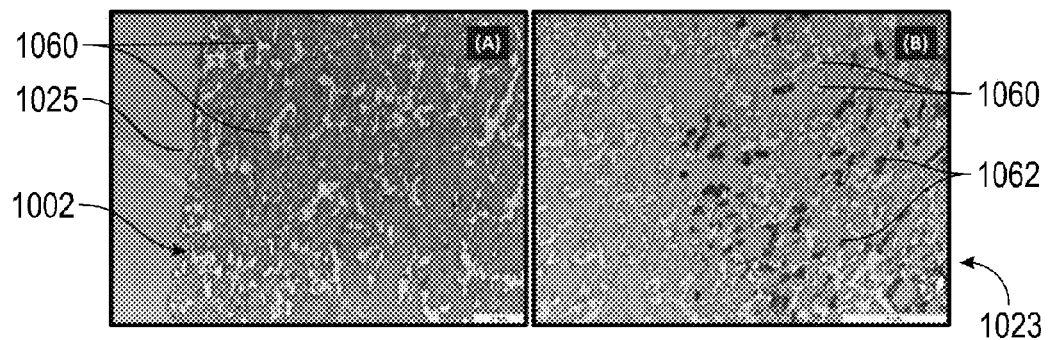
FIGS. 10A and 10B are transmission electron microscopy (TEM) images of the hollow fiber of FIGS. 9A and 9B according to an embodiment.

As can be seen in FIGS. 10A and 10B, the regions of light gray shade 1060 are pores in the hollow fiber 1002, and dark spots 1062 are stained cells. FIG. 10A shows an area in the vicinity of an outer surface 1025 and FIG. 10B shows an area near an inside surface 1023. As is evident, cells 1062 are only observed near the inside surface 1023 of the hollow fiber 1002.

EXAMPLE 6

Comparison of Inoculation Techniques

Minimal growth medium was prepared as described in Example 2.

A comparison of the two inoculation methods, namely filter-type inoculation and incubation-type inoculation, was performed on ultrafiltration membrane discs (Millipore XM50, EMD Millipore, Billerica, Mass.) made of the same polyacrylonitrile/PVC polymer as the hollow fiber bundle bioreactor discussed in Example 12. The membrane discs were inoculated with R. eutropha (Re2061) in the spongy layer using filtration technique in a 47 mm stainless steel syringe filter holder (XX4404700, EMD Millipore, Billerica, Mass.) or via an incubation method which involved submerging the membrane disc pieces in tryptic soy broth medium containing R. eutropha (Re2061).

Figure 11:
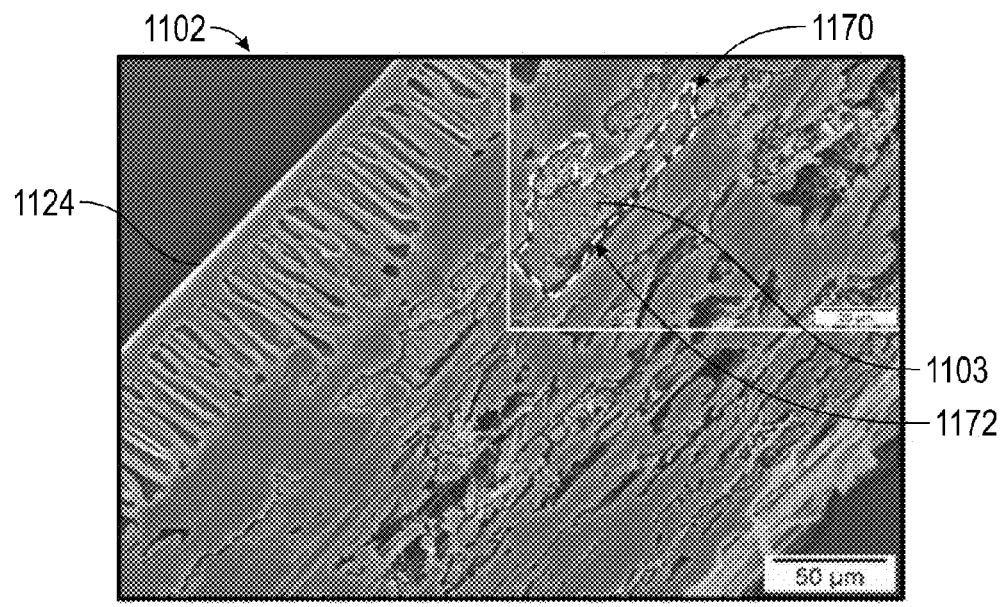
FIG. 11 is an SEM image of a cross section of a polyacrylonitrile-PVC copolymer membrane hollow fiber inoculated by filtration according to an embodiment.

FIG. 11 is an SEM image of a cross section of the hollow fiber following filtration inoculation, in which 10 ml medium containing R. eutropha (Re2061) (OD600=4.7) was pumped through the filter using a syringe under pressure at about 15 $lb_f/in^2$ (1.02 atm) After the filtration, 10 ml clear filtrate is collected. The membrane disc was rinsed with 25 ml distilled water before being prepared for SEM. Area 1170 shows cells 1103 packed into a macroporous structure 1172 of the fiber wall 1124.

Figure 12:
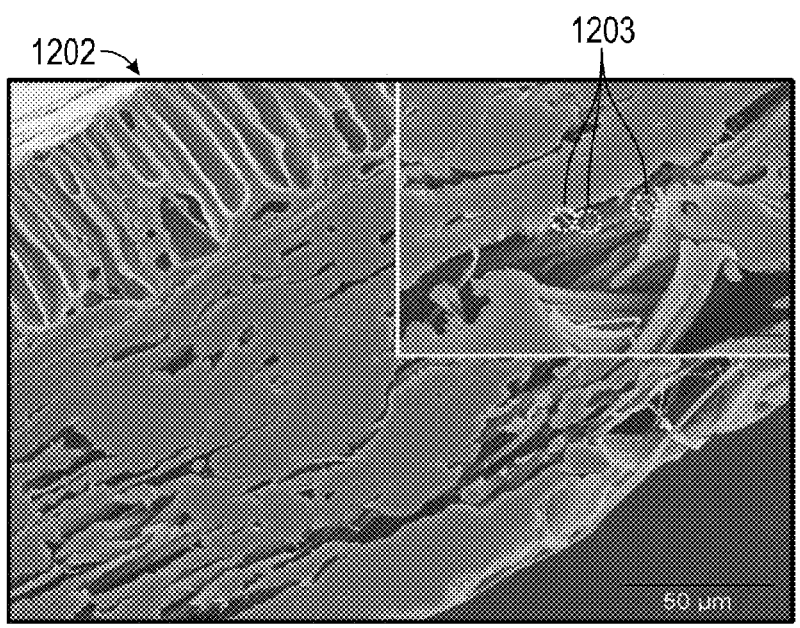
FIG. 12 is an SEM image of cross section of a porous fiber wall inoculated by incubation according to an embodiment.

FIG. 12 is an SEM image of cross section of the hollow fiber inoculated by the incubation technique, where membrane disc pieces were incubated in 2 ml tryptic soy broth medium inoculated with R. eutropha (Re2061) until the OD600 reached 4.

Individual cells 1203 can be seen scattered on the interior surface of the macroporous structure 1172 of the fiber wall 1124.

The relative amounts of cells retained by the membrane for the two inoculum methods was quantitated by protein content of the cells using fluorescamine assay described in Example 5 In this case, XM300 membrane discs (EMD Millipore, Billerica, Mass.) were used. Inoculation of the membrane (cut to 47 mm in diameter) by filtration was done by pushing 25 ml R. eutropha (Re2425/pJL26) culture in minimal growth medium across the membrane under 30 $lb/in^2$ (2.04 atm) pressure. After the filtration, 25 ml filtrate was collected, and the OD600 was determined to be 0.23. Another piece of membrane of equal size was inoculated by submerging it in 50 ml minimal medium inoculated with R. eutropha (Re2425/pJL26) until OD600 reached 3.4. The filter discs were rinsed with distilled water before protein quantitation.

Figure 13:
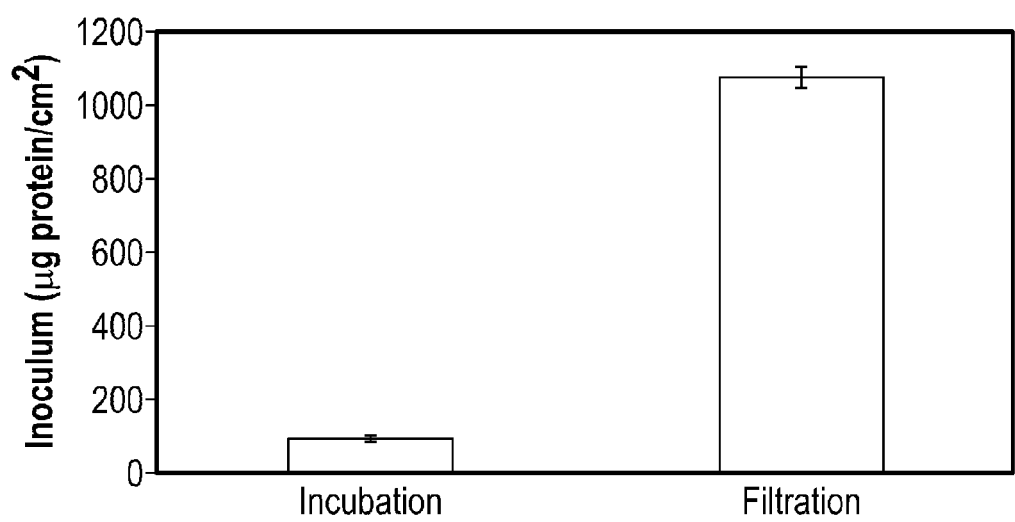
FIG. 13 is a graph comparing inoculation achieved by incubation and filtration according to various embodiments.

As FIG. 13 shows, the filtration method achieved a much higher inoculum (initial microbial cell density) than the incubation method.

EXAMPLE 7

Multi-Fiber Bioreactor

Figure 14:
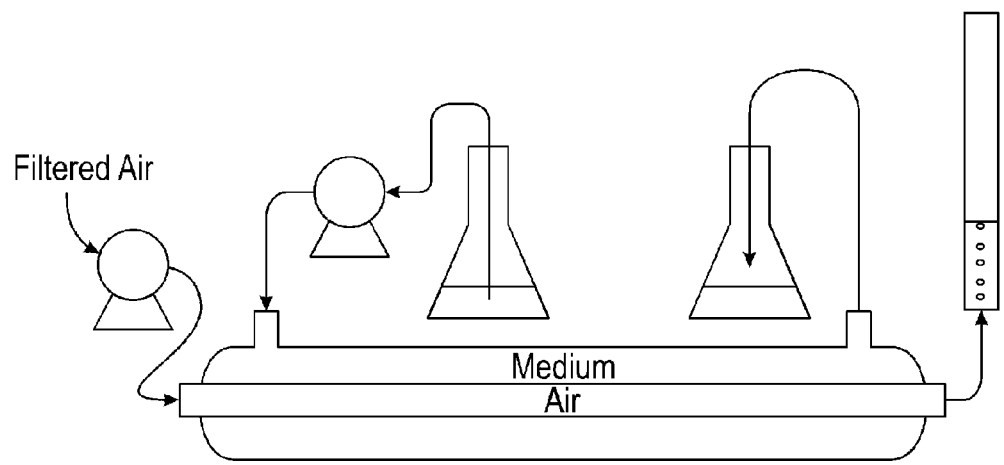
FIG. 14 is a schematic illustration of a system configuration for heterotrophic operation which includes a multi-fiber module according to an embodiment.

The single-fiber experiment of Example 6 was scaled up to a 14-fiber mixed cellulose ester (ME) hollow fiber module. (Product number X32M-601-02N Spectrum Laboratories, Inc. Rancho Dominguez, Calif.). FIG. 14 is a schematic representation of the module as it was used in this testing. The module had a total surface area, i.e., total area of fiber walls comprised approximately 180 cm². The water column attached to a gas outlet was used to maintain a back pressure on the gas in the fiber lumen in order to prevent the liquid (from flowing into the gas stream.

The fiber was inoculated from the inside out by pumping a microbial cell suspension into the fiber lumen at a pressure sufficient to force liquid through the fiber wall and out through the shell side. (FIG. 4). Because the cells were larger than the pores of the fiber wall, they were filtered onto and/or within the fiber wall. Since previous microscopic examination showed that pores on the shell side of the fibers were considerably smaller than on the lumen side and too small to allow microbial cell penetration into the spongy layer, inoculation was performed from the lumen side in this testing to prevent significant microbial cell growth in the minimal medium. The module was then operated with a continuous flow of the sterile minimal medium that would promote microbial cell growth promotes bioproduct formation through the shell side at 10 ml/min and continuous flow of sterile air at 50 ml/min through the lumen.

To help prevent growth of contaminants, all components and media were autoclaved for 20 min at 121° C., all gases were filtered (Millex-HA Filter Unit, EMD Millipore, Billerica, Mass.) in-line prior to entering the bioreactor. 10 m/ml gentamicin (J. R. Scientific, Woodland, Calif.) was added to the minimal medium.

Microbial cell growth in the shell side heterotrophic medium was observed after about two days, and a biofilm was clearly visible on the outside of the fibers after 12 days as a cream-colored residue on and between the white hollow fibers. At the end of the experiment, an attempt was made to rinse the biofilm off the fibers by repeatedly pumping buffer (phosphate buffer saline pH 7.4) through the shell side at a relatively high interstitial velocity (about 30 cm/s). Despite this flushing, most of the biofilm remained attached to the fiber surface (See schematic in FIG. 2).

The presence of cells in the shell side suggests microbial cell transport occurred through the 0.2 μm nominal pore size fibers. This may have occurred as a result of the high pressure inside-out filtration inoculation strategy and/or the presence of at least one pore path sufficiently large to allow microbial cell leakage to the shell side.

EXAMPLE 8

Figure 15:
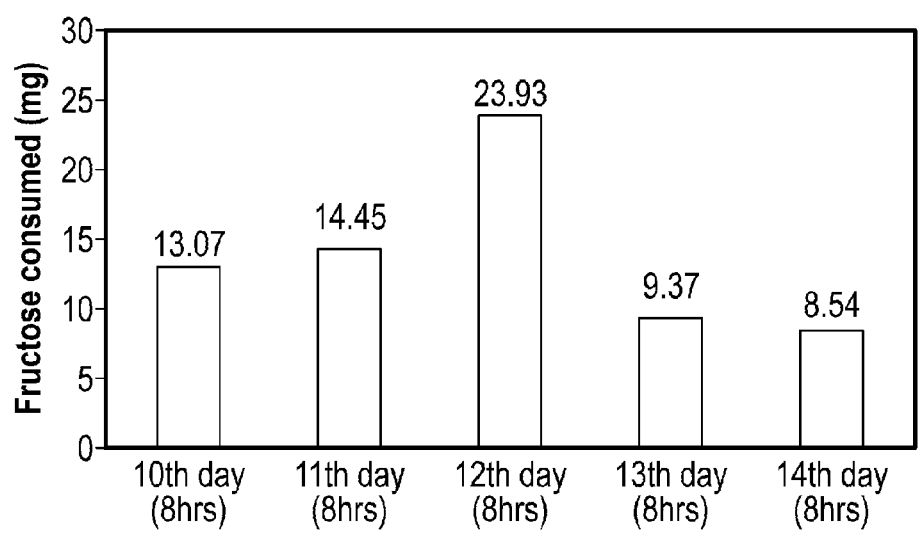
FIG. 15 is a graph showing fructose consumption during operation of a multi-fiber bioreactor according to an embodiment.

The procedure described in Example 6 was used to measure the rate of *R. eutropha* growth on fructose inside the fiber wall of the mixed cellulose ester fiber. Fructose consumption was measured periodically by stopping flow of the heterotrophic growth medium (i.e., heterotrophic minimal medium) through the shell side and the measuring the change in fructose concentration over a fixed period of time (e.g., 8 h), i.e., measuring the initial and final fructose concentration before and after the media flow is stopped for 8 h. Fructose consumption increased through Day 12 and then decreased as shown in FIG. 15. The expected increase in fructose consumption growth of the fructose-consuming biofilm on and within the spongy layer and the unexpected decrease, to excessive microbial cell growth, which caused the fibers to become clogged with biofilm. Clogging blocked air flow, thus blocking access of the cells to oxygen, thus slowing their metabolism. Confirmation of fiber lumen blockage by biofilm growth was confirmed by SEM as shown in FIGS. 16A-16D.

Figure 16A:
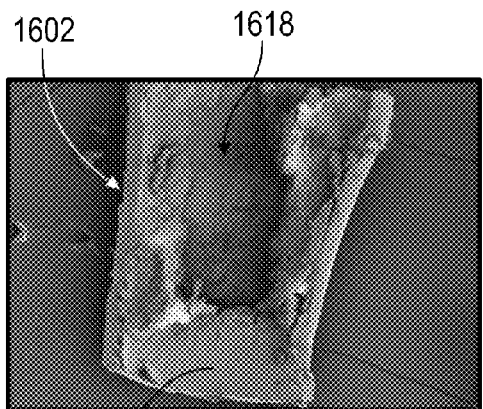
FIGS. 16A, 16B, 16C and 16D are SEM images of cell growth in a lumen side of a hollow fiber according to an embodiment.
Figure 16B:
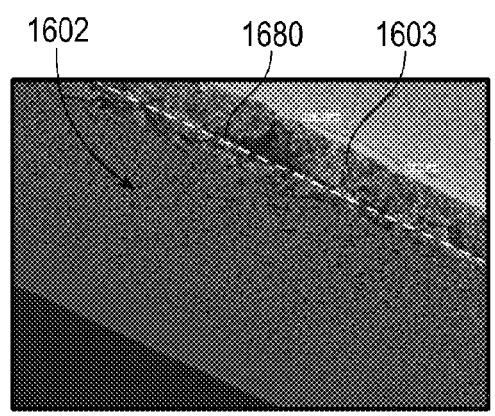
Figure 16C:
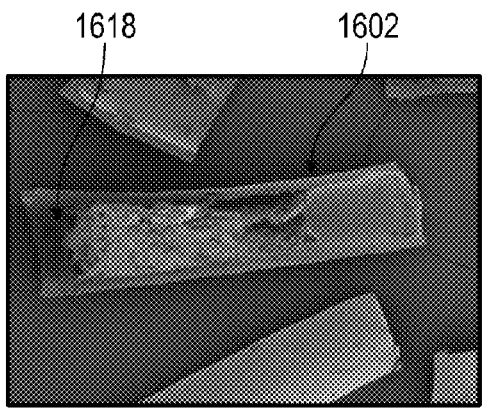
Figure 16D:
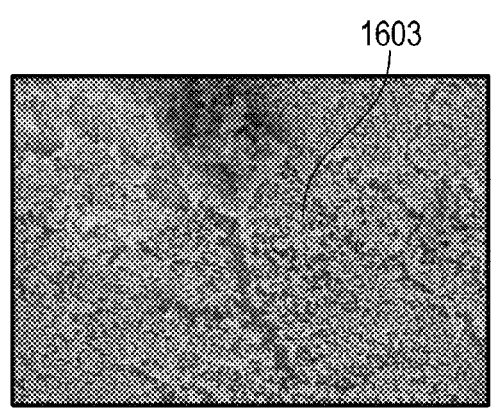

FIGS. 16A and 16B show the fibers 1602 which were cut lengthwise to expose the microbial cell mass in the lumen 1618. The biofilm 1603 was thick enough in some places to plug the lumen 1618 and block the air flow. The white dashed line 1680 indicates the boundary between the hollow fiber 1602 and the biofilm 1603. FIG. 16C provides a cross sectional view of the fiber 1602. The biofilm 1603 in this image measured 33 μm thick. FIG. 16D shows the biofilm 1603 which had a microbial cell density sufficiently high such that the bioreactor's volumetric reaction rate is not limited by the cell density.

EXAMPLE 9

Preliminary Continuous Operation of the 14-fiber Bioreactor with Gas Feed ($H_2$, $CO_2$ and $O_2$)

The 14-fiber bioreactor used in Examples 6 and 7 was inoculated with 50 ml of *R. eutropha* (OD600 of 4) using inside-out filtration (shown in FIG. 4 and described in FIG. 4 and Example 5. The lumen was rinsed with 32 ml sterile water to wash off loosely attached cells.

The pH, temperature and dissolved oxygen level of the production medium was controlled by Sartorius fermenter. The media was circulated in the lumen side to achieve uniform flow conditions.

Figure 17:
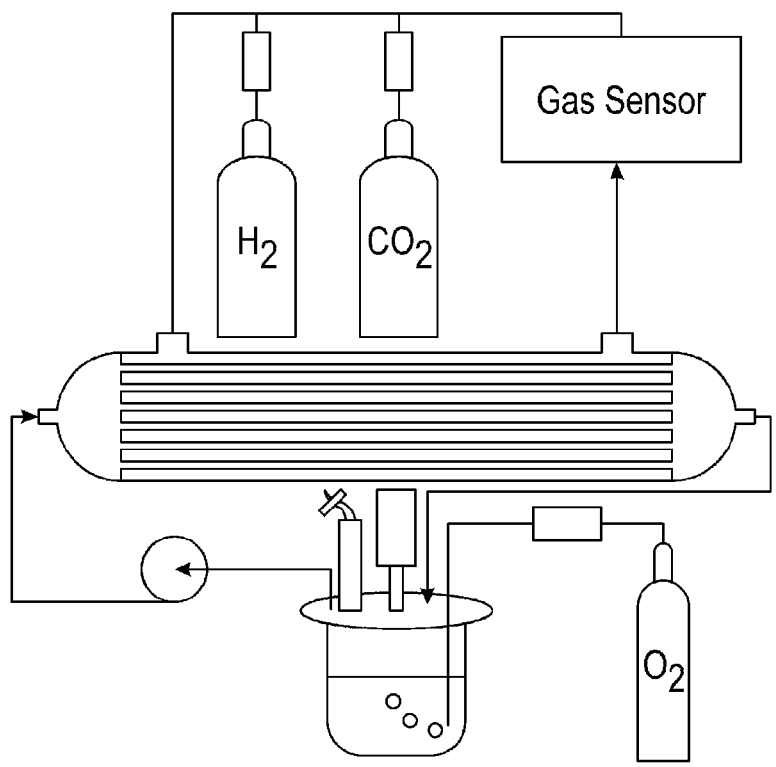
FIG. 17 is a schematic illustration of a system configuration for autotrophic operation according to an embodiment.

FIG. 17 shows the system configuration for autotrophic fermentation. After eight days of heterotrophic growth, autotrophic operation was initiated by circulating minimal media containing no fructose and low nitrogen (0.01% $NH_4Cl$) through the lumen side and pumping a mixture of hydrogen and carbon dioxide at a 5:1 ratio in the shell side. The heterotrophic minimal medium containing 2% fructose (prepared as described in Example 2) was circulated in the hollow fiber lumen from the fermenter, where the dissolved oxygen concentration and pH were maintained. A mixture of $H_2$ and $CO_2$ was circulated in the shell side at a 5:1 ratio while filtered air was fed through the lumen side without recycling. The gas was recirculated by a diaphragm pump located in a gas sensor unit, namely the ENMET gas sensor, (ENMET GSM-60, Ann Arbor, Mich.).

Figure 18:
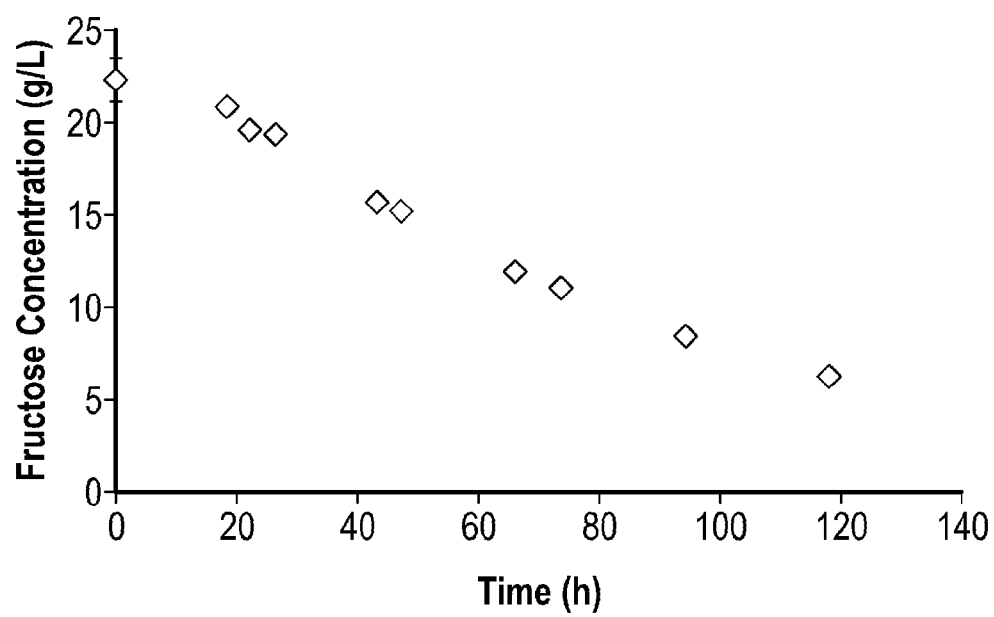
FIG. 18 is a graph showing fructose consumption during heterotrophic growth phase according to an embodiment.

Samples were taken periodically from the reservoir to monitor the fructose consumption during heterotrophic growth stage. As FIG. 18 shows, about 80% of the fructose was consumed within about 120 h. Shortly after the medium was introduced to the lumen side, the medium in the fermenter became turbid; indicating at least part of the biofilm was sheared off from the hollow fiber surface.

During the 6 days of autotrophic operation, no IBT was detected in the fermenter, with SEM images (not shown) showing relatively few cells on the interior surface, suggesting that much of the biofilm formed during the heterotrophic growth stage was sheared off during the start-up of autotrophic operation phase. The shear stress due to laminar flow of the autotrophic medium at the volumetric liquid flow rate of 16 ml/min was calculated to be about 2 dyne/cm² within the bioreactor, which is typically considered a relatively low shear force for biofilms.

In order to reduce shear stress experienced by the cells, a second autotrophic experiment was carried out with the bacterial cells immobilized on the exterior surface of the hollow fibers by filtration. The exterior surface was in contact with the gas phase during autotrophic conditions. 50 ml of *R. eutropha* culture (Re2061) (OD600 of 4) was used for inoculation. After 12 days of heterotrophic growth, the autotrophic operation was initiated in the same configuration as described above, with the addition of a cold trap to help condense any IBT that may have evaporated. Samples were taken from both the fermenter and the cold trap and analyzed for IBT. However, no IBT was detected during 8 days of autotrophic operation.

There are several possible reasons why no IBT was detected during this preliminary testing. The microbial cell mass retained in the fiber wall may not have been high enough to produce IBT at detectable levels. Additionally or alternatively, IBT may have been produced autotrophically in one region of the bioreactor where $H_2$, $O_2$ and $CO_2$ were available but was consumed heterotrophically in another region by cells lacking $H_2$ and/or $CO_2$. Additionally or alternatively, IBT may have been formed, but then evaporated and was removed from the bioreactor in the gas phase. Additional testing with alternate strains of R. eutropha will be conducted as discussed in Example 12.

EXAMPLE 10

Measurement of Diffusion Coefficients for Gaseous Components in Hollow Fiber

The diffusion coefficients for oxygen and carbon dioxide mass transfer between the tube-side liquid and fiber wall were measured. Since the gaseous nutrients were supplied to the biofilm by diffusion, measuring the diffusivities of the gases in the membrane contributed to the validation of the mathematical model which can then be used to optimize operating conditions for the bioreactor system.

Figure 19:
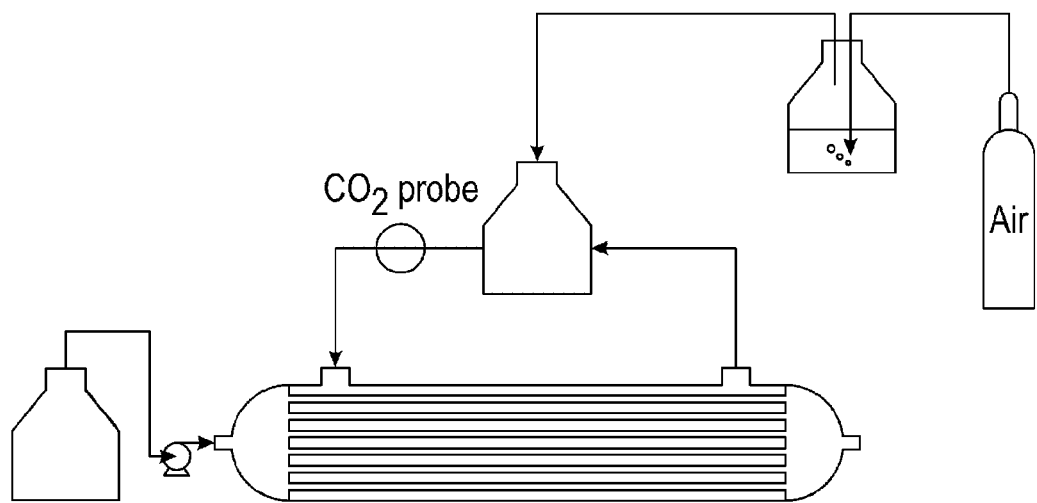
FIG. 19 is a schematic illustration of a system for measuring carbon dioxide mass transfer between gas phase in a shell portion of a bioreactor and an aqueous phase circulating through a lumen side according to an embodiment.

The process of carbon dioxide dissolution in water is complicated by the formation and dissociation of carbonic acid. As more carbon dioxide diffuses into water, the pH changes, and the rate of dissolution can be controlled by the rate of bicarbonate formation from dissolved carbon dioxide. The dissolution rate can be accelerated by dissolving alkaline reagents in the water, but doing so can cause unrealistically high reaction rates due to rapid chemical reactions within the liquid film. To avoid these complications, a system was developed which is shown schematically in FIG. 19.

Reverse-osmosis purified water that has been equilibrated with air (21% oxygen, 79% nitrogen) is pumped through the lumen without recirculation while a fixed amount of gas having an initial composition of 5% carbon dioxide, 21% oxygen and the balance nitrogen is recirculated though the shell side. Changes in the carbon dioxide concentration in the gas phase are then monitored as a function of time using a gas-phase carbon dioxide sensor.

Since the liquid is in equilibrium with 21% oxygen, there is no driving force for oxygen mass transfer between the gas and liquid phase. Because Henry's law coefficient of nitrogen (1639 L·atm/mol) is much greater than that of carbon dioxide (29.4 L·atm/mol) (38), the flux of nitrogen desorbed into the gas is much smaller than that of carbon dioxide adsorption and can be neglected. As carbon dioxide is adsorbed into the liquid stream, the total amount of gas in the reservoir is reduced. To avoid a reduction in pressure, the reservoir is connected to an air cylinder with a water trap that releases air into the chamber as the carbon dioxide is consumed. Using this set up, we maintained a virtually zero carbon dioxide concentration in the liquid phase and measured the rate of decrease in carbon dioxide content without having to consider the reaction of carbon dioxide with water.

An unsteady-state mass balance on carbon dioxide in the gas phase was developed to calculate the apparent diffusion coefficient for carbon dioxide in the hollow fiber membrane. The mass balance was based on the assumptions that the water liquid in the system had a constant volume and was well mixed, and that the axial carbon dioxide concentration gradient along the hollow fibers was negligible. The liquid flow rate was maintained at high enough values that these assumptions were valid. The "dead volume" in the tubing connecting the reservoir and hollow fiber lumen was also minimized.

Integrating the mass balance equation gave Equation (1), which predicts that the natural log of carbon dioxide concentration should follow a linear relationship with respect to time, with carbon-dioxide-free water flowing in the lumen), and that the slope can be used to calculate the apparent diffusion coefficient of oxygen across the spongy layer (D).

$$\ln C_{CO_2} = -\frac{DA_{membrane}}{\Delta r V_{total}} \cdot t + \text{constant} \qquad (1)$$

In Equation (1), D is the apparent diffusion coefficient of carbon dioxide between the liquid stream and gas phase in the shell side, $A_{membrane}$ is the hollow fiber membrane surface area, $\Delta r$ is the thickness of spongy layer of the hollow fiber, and $V_{total}$ is the total gas volume in the system (shell, tubing, and reservoir). The slope was determined using linear regression and then used to calculate the corresponding D value. The process was repeated three times for each of four different liquid flow rates (Table 1).

TABLE 1

Apparent diffusion coefficients for carbon dioxide transport across the spongy layer of the hollow fiber membrane.

| Liquid Flow Rates (ml/min) | Measured $D_{app}$ for $CO_2$ (cm$^2$/s) |
|---|---|
| 15 | 3.33 × 10$^{-6}$ ± 0.07 × 10$^{-6}$ |
| 49.2 | 4.56 × 10$^{-6}$ ± 0.08 × 10$^{-6}$ |
| 73 | 5.05 × 10$^{-6}$ ± 0.32 × 10$^{-6}$ |
| 100 | 5.12 × 10$^{-6}$ ± 0.39 × 10$^{-6}$ |

The measurement of oxygen diffusion coefficients in the hollow fiber membrane was repeated for the same flow rates, and the results are listed in Table 2.

TABLE 2

Apparent diffusion coefficients for oxygen transport across the spongy layer of the hollow fiber membrane.

| Liquid Flow Rates (ml/min) | Measured $D_{app}$ for $O_2$ (cm$^2$/s) |
|---|---|
| 15 | 9.76 × 10$^{-6}$ ± 5.41 × 10$^{-7}$ |
| 49.2 | 1.20 × 10$^{-5}$ ± 8.74 × 10$^{-7}$ |
| 73 | 1.43 × 10$^{-5}$ ± 1.06 × 10$^{-6}$ |
| 100 | 1.46 × 10$^{-5}$ ± 3.18 × 10$^{-7}$ |

The results showed that the diffusion coefficient is affected by the liquid flow rate at low flow rates, but the effect decreases as the flow rate rises. This phenomenon could be caused by the shrinking diffusion boundary layer in laminar flows. As demonstrated in FIG. 31, the apparent diffusion resistance across the hollow fiber membrane consists of resistance across the membrane $$\left(\frac{L}{D_{membrane}}\right)$$

and across a diffusion boundary layer on the membrane $$\frac{1}{(k)}$$

(Equation 2). L is the thickness of membrane; $D_{app}$ is the apparent diffusivity; $D_{membrane}$ is the diffusivity in the membrane, and k is the mass transfer coefficient, which is affected by the liquid velocity. At low liquid flow rates, the mass transfer coefficient is small, and the diffusion boundary layer is rate limiting, but as the flow rate is raised, the boundary layer becomes thinner, causing mass transfer coefficient k to increase and eventually ceasing to limit the overall rate of diffusion.

The impact of liquid flow rate on diffusion resistance across the diffusion boundary layer can be described by an empirical correlation of Sherwood number (Sh) and Reynolds number (Ra) for laminar flow in a pipe (10) (Equation 3-4), where L is the membrane thickness; D is the oxygen diffusivity in water; μ is the local viscosity of fluid while $\mu_w$ is the average viscosity; ρ is the density of fluid; d is the diameter of fiber; v is the fluid velocity and L is the fiber length. Given this correlation and the measured diffusion coefficients at various flow rates, the membrane diffusivity can be extracted by fitting experimental data to Equation 1. The dash lines in FIGS. 32 and 33 represent the simulation results, which show a similar trend as found in experimental results.

$$\frac{L}{D_{app}} = \frac{L}{D_{membrane}} + \frac{1}{k} \quad (2)$$

$$Sh = \frac{kd}{D} = 1.62\left(\frac{d^2 v_0}{LD}\right)^{1/3} \quad (3)$$

$$Re = \frac{\rho v d}{\mu} \quad (4)$$

The apparent diffusion resistance across the porous fiber wall (i.e., membrane), comprises resistance across the membrane $$(\frac{L}{D_{membrane}},$$

Figure 20:
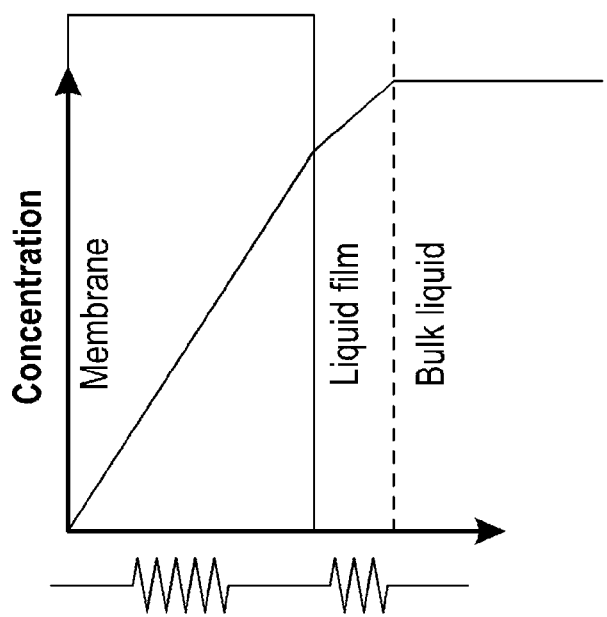
FIG. 20 shows diffusion across a porous fiber wall according to an embodiment.

L is the thickness of membrane and $D_{membrane}$ is the diffusivity in the membrane) and a stagnant liquid film on the membrane (the reciprocal of mass transfer coefficient k) (FIG. 20). The liquid film gets thinner as the liquid flow rate rises, and its resistance to diffusion becomes insignificant at very high flow rates.

EXAMPLE 11

Development of Economical, Surfactant-free Microbubble Generator

Two types of microbubble generators were developed and characterized. Specifically, a swirling-flow generator was made from 1.25 in (3.12 cm) PVC pipe and a pipe-threaded inlet tube. An ejector-type generator was made from ¼ inch ID stainless steel tube 21 cm long with a 12 cm stainless steel tube protruding midway from the side. A large-capacity peristaltic pump capable of delivering water at a flow rate of about 6 L/min was used to generate sufficiently high velocity inside the generators to generate microbubbles. The use of a peristaltic pump provides the opportunity for aseptic operation at the small scale.

Figure 21:
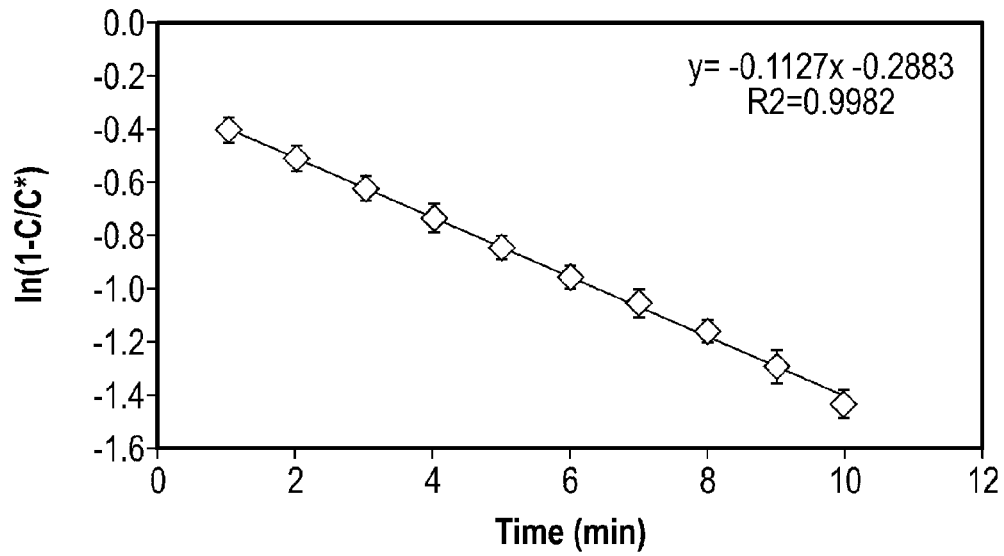
FIG. 21 shows is a graph showing data used to determine $k_L a$ value of a microbubble dispersion according to an embodiment.

Volumetric mass transfer coefficients ($k_L a$) were measured for the home-made microbubble generator systems in a 20 gallon (75.7 L) aquarium that used an axial flow mixer to achieve slow recirculation of the microbubble dispersion throughout the aquarium. The aquarium water contained 1% NaCl to discourage bubble coalescence. After microbubble sparging was initiated, dissolved oxygen concentration was measured as a function of time. A mathematical model of the unsteady state mass transfer (not shown) predicted that plotting the data in a semi-log format should give a straight line with a slope equal to the $k_L a$ value. An example of the experimental data used to determine a $k_L a$ value of 0.1127 min$^{-1}$ (6.6 h$^-$) is shown in FIG. 21. Error bars represent standard deviation of the duplicate measurements. The highly linear trend ($R^2$=0.9982 for a linear fit) validated the mathematical model.

At a gas flow rate of 0.15 L/min, $k_L a$ values for air sparging were 8.4 h$^{-1}$ (plastic) and 6.6 h$^{-1}$ (metal). The corresponding values for $N_2$ sparging were 4.0 h$^{-1}$ (plastic), 3.9 h$^{-1}$ (metal). The higher values achieved for air sparging than for nitrogen sparging may indicate an effect of Laplace pressure, which increases the pressure inside the bubble relative to that outside. During air sparging, oxygen transfer occurs from the bubbles into the liquid, whereas during nitrogen sparging, the oxygen transfer occurs from the surrounding water into the bubbles. A higher intrabubble pressure would increase the driving force for mass transfer from the bubble into the water and would decrease the driving force for mass transfer from the liquid into the bubble. The very low volumetric gas flow rate used for these demonstration experiments was equivalent to 0.0022 volumes of gas/volume of bioreactor-min (vvm). By comparison, vvm values of about 1 are used in highly aerobic, industrial fermenters. Putting the amount of oxygen transferred for the metal microbubble generator using air sparging on the basis of 1 vvm, the equivalent $k_L a$ value would be 6.6 h$^{-1}$(1/0.0022)=3000 h$^{-1}$. This result suggests that our simple system consisting of home-made microbubble generator and peristaltic pump will be able to provide high oxygen mass transfer rates in the lumen of our hollow fiber bioreactors.

Figure 22:
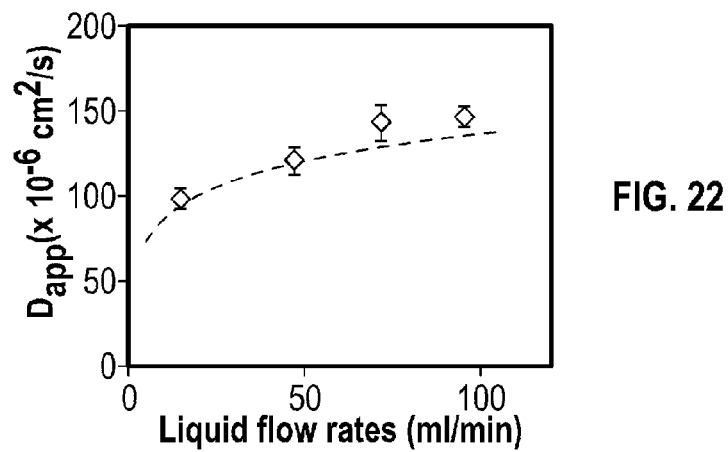
FIG. 22 shows calculated apparent diffusion coefficients of oxygen at different liquid flow rates according to various embodiments.

FIG. 22 shows calculated apparent diffusion coefficients of oxygen at different liquid flow rates with simulated correlation between apparent diffusion coefficients and liquid flow rates.

Figure 23:
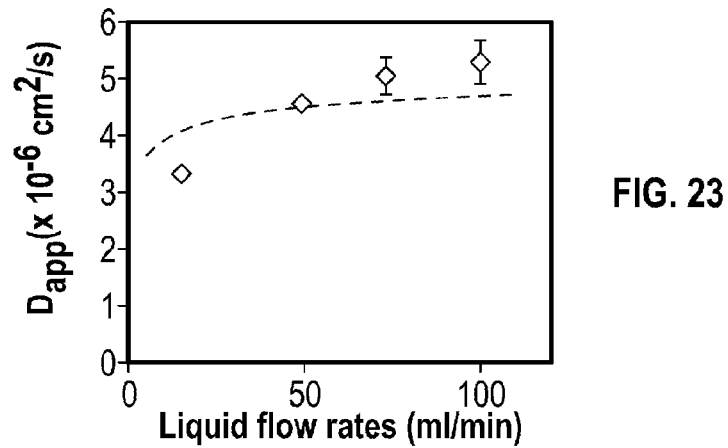
FIG. 23 shows calculated apparent diffusion coefficients of carbon dioxide at different liquid flow rates according to an embodiment.

FIG. 23 shows calculated apparent diffusion coefficients of carbon dioxide at different liquid flow rates with simulated correlation between apparent diffusion coefficients and liquid flow rates.

EXAMPLE 12

Figure 24A:
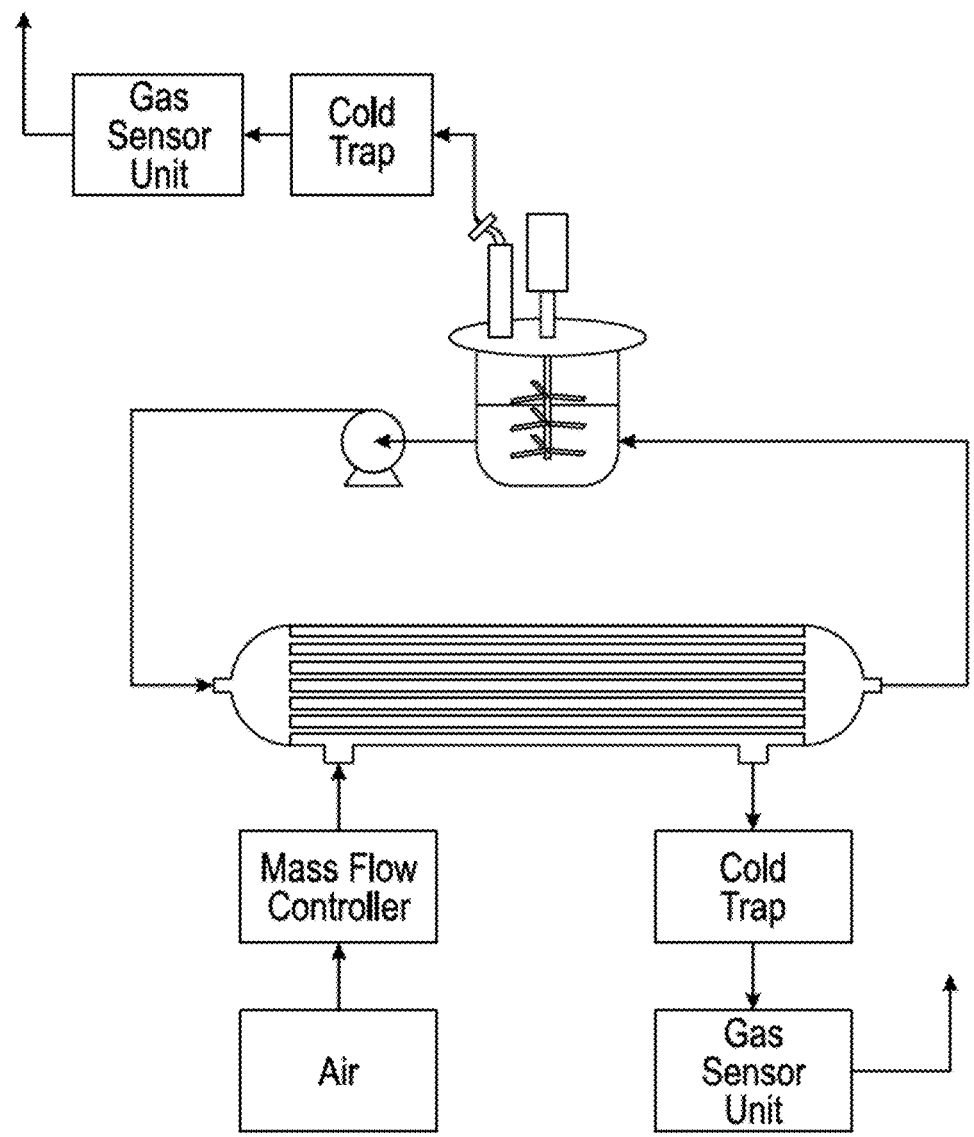
FIG. 24A is a schematic illustration of another system configuration for heterotrophic fermentation with flow-through configuration on the shell side according to an embodiment.

This example demonstrates use of a hollow-fiber bioreactor for continuous autotrophic production of IBT from $H_2$, CO$_2$ and O$_2$ using the configuration shown in FIG. 24A. The hollow fiber bundle bioreactor (Romicon ultrafiltration cartridge HF, 1018-1.0-45-XM50) was purchased from Koch Membrane System, Inc., Wilmington, Mass. The fibers (hereinafter "fiber module") in the bioreactor are made from a polyacrylonitrile-PVC copolymer membrane. The fiber module was chemically sterilized following manufacturer's instructions. Sodium hypochlorite (NaClO) solution (500 ppm, 300 mL) was pushed across the membrane using a 60 mL syringe, before the fiber module's lumen and shell space were filled with the solution and the fiber module was incubated for at least 2 h. Afterward, the fiber module was rinsed repeatedly with sterile water to remove residual NaClO.

*Ralstonia eutropha* (Re2425/pJL26/pJL26) cells obtained from Anthony Sinskey, Department of Biology, MIT, were cultivated in 50 mL heterotrophic minimal medium (as described in Example 2) until they reached exponential growth phase before immobilization (OD600=0.18). The fiber module was inoculated using a filtration method, in which the exponentially growing culture of recombinant *R. eutropha* capable of producing IBT (See Brigham, supra), was pumped into the shell side at a gauge pressure of 15 lb/in$^2$ (1.0 atm). The pressurization was achieved using sterilized compressed air.

During inoculation, the concentrated culture was pumped through both of the shell side ports, such that liquid was forced through the porous wall of the hollow fibers, depositing cells on and/or within the pores of the fiber wall. The clarified liquid that passed through the walls of the fiber was collected on the lumen side of the fibers.

Figure 24B:
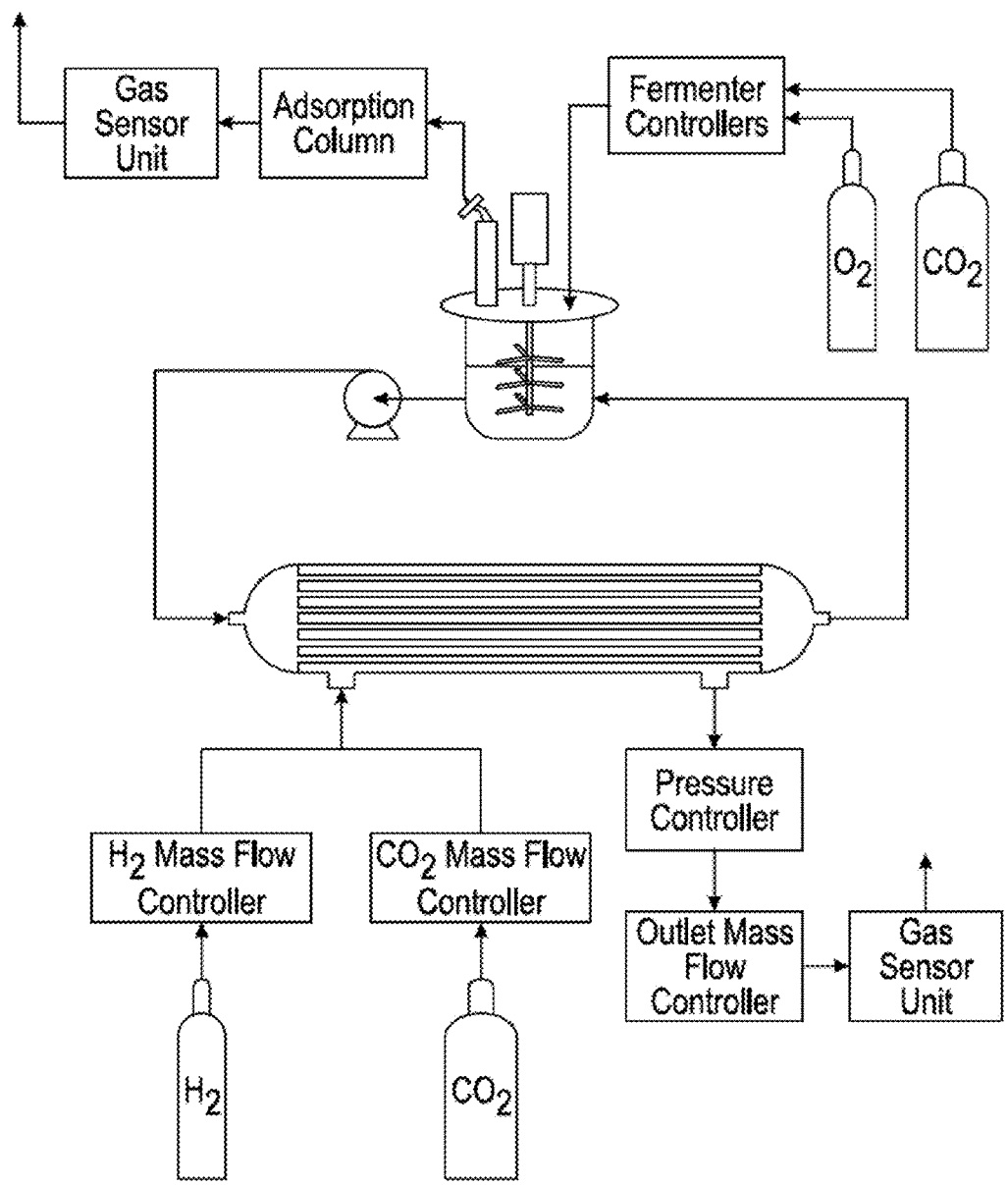
FIG. 24B is a schematic illustration of another system configuration for autotrophic fermentation with flow-through on a shell side of a bioreactor according to an embodiment.

After filtration-inoculation, the hollow fiber module was operated in a heterotrophic microbial cell growth phase according to the schematic shown in FIG. 24B. The operation continued for eight days to encourage additional microbial cell growth on and/or in the porous fiber walls. To facilitate *R. eutropha* growth, a peristaltic pump (Masterflex 7523-00, Vernon Hills, Ill.) was used to deliver 30 mL/min of a heterotrophic minimal medium (described in Example 2) in a recycle mode from 400 mL of minimal medium in the Sartorius fermentor vessel (Sartorius Biostat B Plus, Sartorius Stedim North America Inc. Bohemia, N.Y.) through the lumen side of the hollow fiber bioreactor and then back to the Sartorius bioreactor.

The Sartorius bioreactor fermentor controllers (shown in FIGS. 24A and 24B) regulated the pH, temperature, and dissolved oxygen (DO) concentration of the liquid stream at values of 6.8, 30° C., and 80%, respectively. During the heterotrophic growth phase, air was delivered through the shell side of the bioreactor at a gauge pressure of 5 lb$_f$/in$^2$ (0.34 atm) and a flow rate of approximately 300 mL/min. The pH was regulated by the Sartorius bioreactor's control system via the well-known "automatic-titration method", in which a computer-controlled pump automatically adds 1N NaOH when the pH is too low and adds 1N H$_3$PO$_4$ when the pH is too high. After 8 days, a continuous, autotrophic phase was initiated. The gas in the shell side of the hollow fiber bioreactor was changed to a combination of H$_2$ and CO$_2$ at 0.1 L/min and 0.02 L/min respectively. The H$_2$ and CO$_2$ flow rates were individually regulated using mass flow controllers (FMA6500, OMEGA Engineering, Inc., Stamford, Conn.) in the Opto22-based control network as described in Example 1.

A flow-through configuration was used on the shell side and the exiting gas was sent to a gas sensor unit, namely an ENMET sensor (to monitor O$_2$ contents. The gas was driven by a diaphragm pump located in the ENMET gas sensor unit through the shell side of the hollow fiber and through the shell side of a small glass Friedrichs condenser (Z136808, Sigma Aldrich, St. Louis, Mo.) before measuring the concentrations of CO$_2$ and O$_2$ gases. The measured gas compositions was used to adjust the gas flow rates, if needed, to maintain the desired balance of gases (90 mole % H$_2$ and 10 mole % CO$_2$) in the bioreactor. This gas analysis was also used as a safety precaution to confirm that minimal O$_2$ was found in the shell-side gas stream. The control system was configured such that if unsafe levels of O$_2$ were detected, the H$_2$ feed would have been automatically shut off.

Ethanol cooled to 0° C. in a 1:1 ethylene glycol-water bath was pumped through the lumen side of the condenser as the cooling fluid. The condensate contained water and IBT that had evaporated from the porous fiber wall into the shell side gas phase. Condensate removal provides a method to remove the toxic product (IBT) from the bioreactor to minimize product inhibition of the cells.

A mixture of O$_2$ and CO$_2$ was fed to the medium reservoir in a 9:1 ratio. The gas flow rate into the reservoir was regulated by the Sartorius control tower to maintain dissolved O$_2$ (DO) level at 80% of air. To minimize IBT loss due to gas stripping in the Sartorius vessel, an IBT cold trap was attached to the reservoir exhaust. A second ENMET gas sensor was installed to monitor the gas composition of the exhaust gas exiting the reservoir vent.

During both heterotrophic and autotrophic bioreactor operations, the condensate from the two condensers and the liquid in the Sartorius fermentor was assayed for IBT using gas chromatography (GC). The GC was calibrated using standard solutions of IBT so the amount of product formed could be determined quantitatively.

Figure 25:
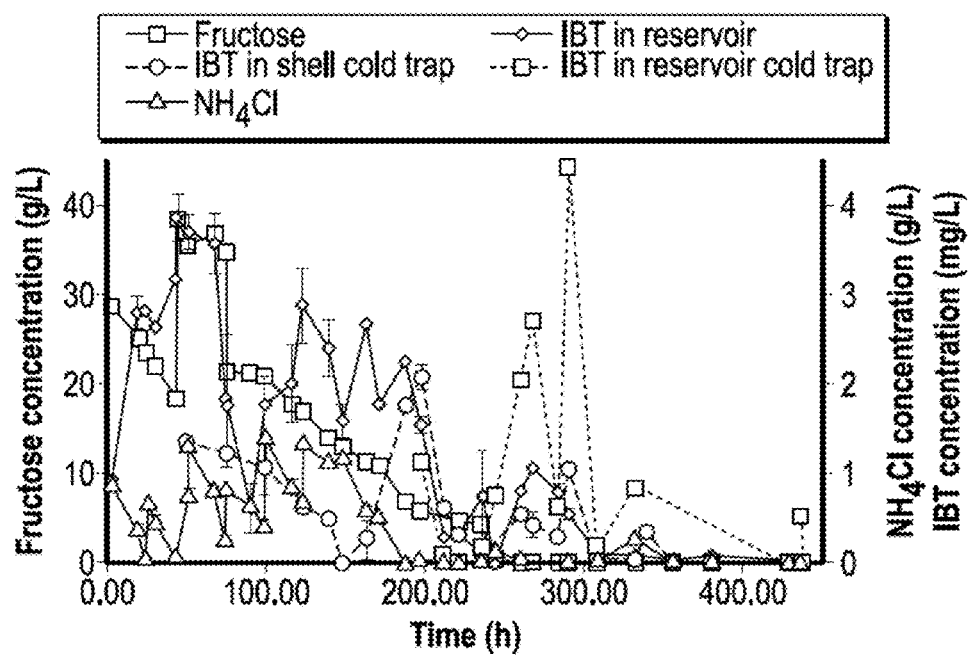
FIG. 25 is a graph comparing isobutanol (IBT), fructose and $NH_4Cl$ concentrations during heterotrophic, mixotrophic and autotrophic stages of a hollow fiber module operation according to an embodiment.

The experimental results are summarized in FIG. 25. Before the autotrophic phase started (0-244 hours, when fructose was present in the liquid medium), IBT was produced, but at low levels, most likely due to the high ammonium concentration maintained to facilitate cell growth on fructose. Ammonium concentration is known to affect the carbon flux in *R. eutropha*'s metabolic network. Cell growth requires a nitrogen source but the pathway engineered to produce IBT does not. A high ammonium concentration results in most of *R. eutropha*'s carbon source being channeled towards cell growth, thus limiting the carbon availability to IBT formation. Protein quantitation showed that the total immobilized cell mass grew from 1.56±0.02 to 4.22±0.58 g DCW during the entire experiment, and most of the growth likely occurred during the heterotrophic phase.

After the autotrophic operation was initiated at 168 h, a spike in the IBT concentration in the shell side cold trap was observed, suggesting an increase in the local IBT concentration on the outer surface of the immobilized biofilm. A second increase in the IBT concentrations in both the shell side and reservoir exhaust cold trap was observed right after the liquid in the culture was replaced with fructose-free medium at 244 hour, providing preliminary evidence of IBT autotrophic production in the BIG system. The IBT concentration in the liquid reservoir reached a maximum of 1.05 mg/L at hour 268. The increased IBT concentration was accompanied by a drop in ammonium concentration from 0.13 g/L to 0 g/L. Low ammonium levels induce higher carbon flux through the IBT-production pathway. (See, for example, Lu J, et al., October 2012. Studies on the production of branched-chain alcohols in engineered *Ralstonia eutropha*. Applied Microbiology and Biotechnology: 1-15, which is hereby incorporated by reference herein in its entirety.

The measured IBT concentrations were sufficient to confirm continuous, autotrophic IBT production and verify that the bioreactor for incompatible gases concept had been reduced to practice.

EXAMPLE 13

With certain configurations, IBT concentrations obtained during continuous, autotrophic IBT production may be lower than expected when relying on reversible enzyme-catalyzed reactions. In the testing described in Example 12, for example, in which high concentrations of *R. eutropha* cells were immobilized in the hollow fibers walls during autotrophic IBT production, it was hypothesized that as these cells consumed the $H_2$ as it diffused through the fiber wall, regions of the hollow fiber furthest from the $H_2$ source (shell side) became $H_2$-limited. It was further hypothesized that cells immobilized in these $H_2$-depleted regions of the fiber then catabolized the IBT produced by cells immobilized in $H_2$-rich regions of the fiber wall, thereby reducing the overall IBT yield. In order to explore this hypothesis, mathematical modeling studies were performed using a commercially available software package, COMSOL Multiphysics. The model incorporates both the reaction kinetics and mass transfer in the hollow fiber bioreactor, and the simulation results successfully reproduced the experimental observations, supporting the hypothesis that the cells consume IBT when the local dissolved $H_2$ concentration is very low.

As such, the testing in this example was designed to ensure the availability of all three gaseous reactants ($H_2$, $CO_2$ and $O_2$) while minimizing loss of unreacted $H_2$ from the bioreactor by using a flow rate leaving the continuous gas phase (i.e., lumen side) approaching zero (i.e., a "dead end" operational mode for the $H_2$). In this testing, planktonic *R. eutropha* (Re2425/pJL26), i.e., cells were suspended in an aqueous phase and circulated through the shell, as shown schematically in FIG. 26. Pure $H_2$ was delivered to the lumen side using the "dead-end" operational mode described above using a digital back pressure controller (Alicat Scientific, Tucson, Ariz.) installed at the outlet to control the gas pressure within the lumen at 15 psig. The gas flow was increased briefly at designated intervals to flush out any possible gas (such as $N_2$ or $CO_2$) that might otherwise accumulate in the lumen side gas phase and dilute the $H_2$. The vented gas was sent through an ENMET gas sensor to ensure $O_2$ never exceeded a critical level.

Figure 26:
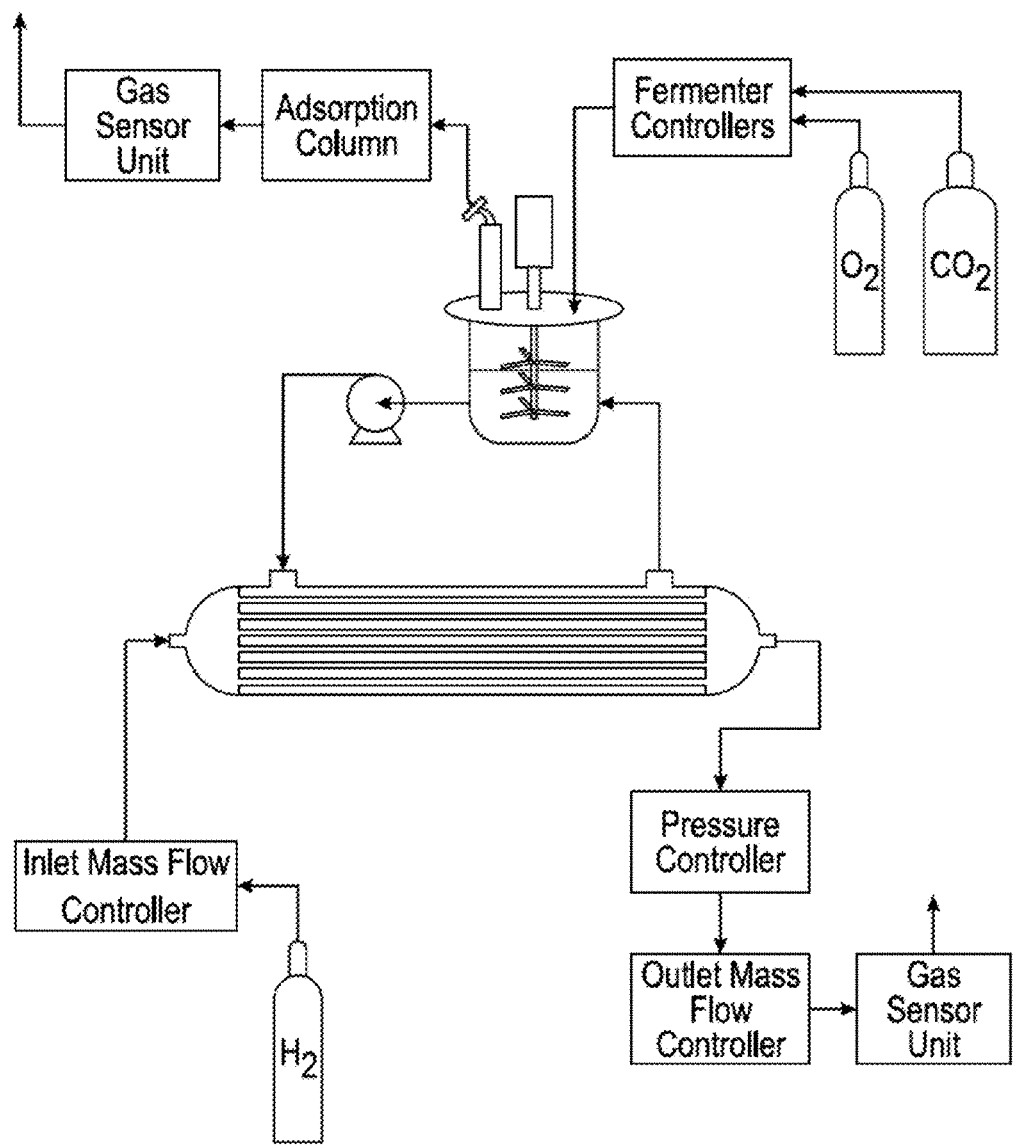
FIG. 26 is a schematic illustration of yet another system configuration for autotrophic fermentation with dead-end configuration on the lumen side of a hollow fiber according to an embodiment.

The Sartorius reservoir's DO was controlled at 80%-100% by sparging a mixture of pure $O_2$ and $CO_2$ gas (0.2-0.3 L/min) through the stirred reservoir, while liquid from the reservoir was pumped through the shell. The vented gas leaving the Sartorius vessel was sent through a gas sensor unit, namely, an ENMET gas sensor, to ensure that $H_2$ never exceeded a critical level. As shown in FIG. 26, an inlet mass flow controller was installed at the lumen inlet and an outlet mass flow controller was installed at the outlet to measure the total amount of gas delivered during the gas-flushing periods. Otherwise, there was no gas flow leaving the lumen side.

After liquid medium had been pumped through the shell side, it was recycled back to the Sartorius reservoir and was directly injected into the liquid already present in the Sartorius reservoir. The system was equipped with a glass column (I.D. 10 mm, length 50 cm, Omnifit®, Diba Industries, Danbury, Conn.) packed with Dowex® Optipore SD-2 polymeric resin (The Dow Chemical Company, Midland, Mich.) to recover IBT from the reservoir effluent gas. Because dilute IBT-in-water solutions are highly nonideal, with IBT having a high relative volatility, cryogenic temperatures were required to achieve virtually complete IBT condensation. As a result, IBT adsorption was found to be a more effective approach for IBT recovery than condensation. The adsorbed IBT was periodically recovered from the adsorption resin using methanol as the desorbent. Two resin columns were alternately used for either capturing IBT or IBT removal and resin regeneration.

The Opto22 control system was programmed to stop $H_2$ flow to the fiber module if the $H_2$ concentration in the exhaust gas from the liquid reservoir exceeded 4%. The ammonia concentration was measured periodically, and $NH_4Cl$ was added as needed to prevent its depletion.

Figure 27:
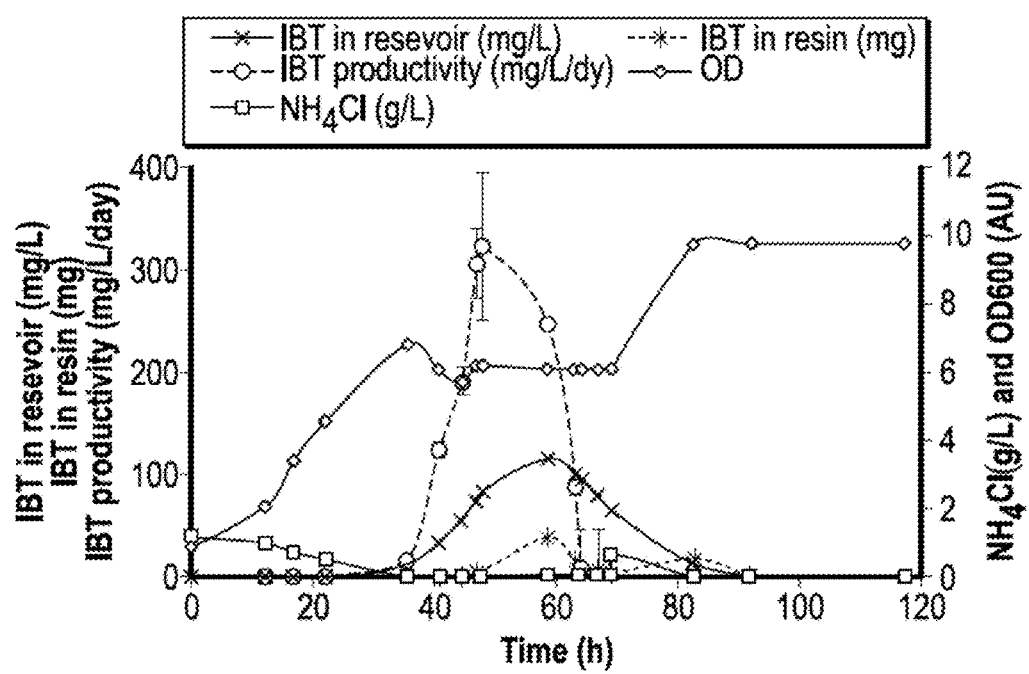
FIG. 27 is a graph showing IBT and $NH_4Cl$ concentrations and cell OD during autotrophic operation with suspended (planktonic) cells according to an embodiment.

The resulting peak IBT volumetric production of was 325 mg/(L day) as shown in FIG. 27. However, when the cell OD reached about 10, the net IBT production plummeted, even under ammonia-limiting conditions. At 92 h, when no apparent IBT production was observed, the $CO_2$ and $O_2$ flow rate into vessel liquid and liquid flow rate through the shell side of fiber module were increased, but no increase in IBT production was detected.

The higher IBT production obtained in experiments that used suspended (planktonic) cells rather than immobilized cells, and the fact that apparent IBT production was not observed at cell density higher than an OD of 10, are consistent with the hypothesis that under $H_2$-limiting conditions, the *R. eutropha* cells catabolized IBT as a carbon and energy source. Additional factors supporting this conclusion include, for example, the observation that the diffusion of $H_2$ across the membrane is slower with immobilized cells, causing $H_2$ transport limitations, and thus product catabolism, to be more prominent. Secondly, $H_2$ mass transfer was enhanced by a higher supply pressure in the experiments with suspended (planktonic) cells than in those using immobilized cells. Additionally, resin adsorption rather than condensation was used to recover IBT with planktonic cells, potentially reducing IBT consumption by the cells.

These results show that a bioreactor configured for use with incompatible gases may be used for continuous product formation while preventing significant gas-phase mixing of incompatible gases both for embodiments that use immobilized cells (Example 12) and embodiments that use suspended (planktonic) cells (Example 13).

The various embodiments described herein provide a bioreactor for producing a bioproduct comprising a housing; and one or more catalytically active zones located in the housing and adapted to keep two incompatible gaseous reactants separated when in the gas phase, wherein each of said catalytically active zones comprises a catalytic component retainer and a catalytic component retained within and/or on the catalytic component retainer. In one embodiment, each of said catalytically active zones additionally or alternatively comprise a liquid medium located on either side of the catalytic component retainer and the catalytic component additionally or alternatively includes a suspended catalytic component suspended in the liquid medium, such that the liquid medium is a catalytically active zone. In one embodiment, a majority of the catalytic component is a suspended catalytic component.

In one embodiment, a liquid medium on a first side of the catalytically active zone is adapted to contain a first gaseous reactant in a form consumable by the catalytic component, and a gaseous medium on an opposing side of the catalytic component retainer is adapted to contain a second gaseous reactant in a form consumable by the catalytic component, wherein the gaseous medium and/or the liquid medium are further adapted to contain a carbon source useful for fermentation. In one embodiment, the carbon source is an autotrophic carbon source. In one embodiment, the fermentation is selected from autotrophic fermentation, heterotrophic fermentation or methanotrophic fermentation.

In one embodiment, there is no autotrophic carbon source (e.g., carbon dioxide) and one of the two incompatible gaseous reactants is both a carbon source and an energy source (e.g., methane, a low water solubility gas). In one embodiment, an autotrophic carbon source is provided in addition to a gaseous reactant that can serve as both a carbon source and an energy source. For example, in embodiments which utilize methane-based fermentations that consume both methane and an amount of carbon dioxide, two gaseous carbon sources (e.g., methane and carbon dioxide) are provided in addition to an energy source (e.g., methane) and one electron acceptor, i.e., a reactant (e.g., oxygen) used by the cells to accept electrons extracted from the energy source during respiration. In one embodiment, the carbon and energy source is highly soluble in water (e.g., fructose).

In one embodiment, the catalytic component retainer comprises one or more porous fiber walls, the catalytic component is a cell culture (e.g., a microbial cell culture) and the bioreactor further comprises a shell area outside the one or more porous fiber walls, wherein each of the one or more porous fiber walls form a hollow fiber which can contain the liquid medium or the gaseous medium therein on the opposing side. In one embodiment, the bioreactor further comprises a cell source to provide the cell to the one or more porous fiber walls for inoculation; and a carbon source to support growth of the cell on the one or more porous fiber walls. In one embodiment, the carbon source is a heterotrophic carbon source and the cell is a bacterium, such as *R. eutropha*.

The bioreactor may further comprise, in one embodiment, a first incompatible gaseous reactant source to provide the first incompatible gaseous reactant to the bioreactor in the liquid medium; and a second incompatible gaseous reactant source to provide the second gaseous reactant to the bioreactor in the gaseous medium. In one embodiment, the first and second incompatible gaseous reactants have low aqueous solubility and the bioreactor further comprises a mass transport enhancer capable of enhancing gas-to-liquid mass transfer of the first and/or second incompatible gaseous reactants into the liquid medium.

The mass transport enhancer may, in one embodiment, be a bubble generator adapted to generate gaseous bubbles (e.g., a microbubble generator 250 (FIG. 2) adapted to generate gaseous microbubbles) in the liquid medium in order to incorporate the first gaseous reactant therein, a bioreactor configuration which allows the catalytically active zone to remain in direct contact with at least one of the incompatible gaseous reactants during operation, or both. In one embodiment, each hollow fiber has an inner diameter and the liquid medium is adapted to flow inside each hollow fiber, wherein most of the bubbles have a diameter smaller than the inner diameter of each hollow fiber.

In one embodiment, the first incompatible gaseous component contains hydrogen and carbon dioxide, the second incompatible gaseous component contains oxygen, and the bioproduct is a C1-C6 alcohol. In one embodiment, the first incompatible gaseous component contains hydrogen, the second incompatible gaseous component contains oxygen and carbon dioxide, and the bioproduct is a C1-C6 alcohol.

In one embodiment, a first gaseous phase contains hydrogen and carbon dioxide, a second gaseous phase contains oxygen, which is incompatible with hydrogen when mixed in the gas phase, and the bioproduct is a C1-C6 alcohol. In one embodiment, a first gaseous phase contains hydrogen, a second gaseous phase contains oxygen and carbon dioxide, and the bioproduct is a C1-C6 alcohol.

In one embodiment, the bioreactor further comprises a separating system for separating the bioproduct from the autotrophic production mediums and/or a monitoring and control system in communication with the bioreactor.

Various embodiments further provide a method of producing a bioproduct comprising: separating first and second incompatible gaseous reactants in a bioreactor containing a plurality of catalytically active zones, each catalytically active zone comprising a catalytic component retainer and a catalytic component retained within and/or on the catalytic component retainer and/or suspended in a liquid medium located on a first side of the catalytic component retainer; at least partially dissolving a first incompatible gaseous reactant in a liquid medium in contact with a first side of the catalytic component retainer to produce a first compatible reactant; providing a second incompatible gaseous reactant in a gaseous medium to a second side of the catalytic component retainer for consumption by the catalytic component to produce a second compatible reactant; providing a carbon source to at least one side of the catalytic component retainer to support growth of the catalytic component on and/or in the catalytic component retainer; and allowing transport of the first and second compatible reactants in opposing directions through the catalytic component retainer wherein a reaction occurs with the catalytic component to form a bioproduct.

In one embodiment, each catalytically active zone additionally or alternatively comprises a liquid medium located on either side of the catalytic component retainer and the catalytic component additionally or alternatively includes a suspended catalytic component suspended in the liquid medium. In one embodiment, a majority of the catalytic component is the suspended catalytic component.

In one embodiment, the carbon source is provided to the second side of the catalytically active medium. The catalytic component retainer may be, in various embodiments, a hollow fiber and the catalytic component may be introduced into the hollow fiber by an inside-out filtration-type inoculation.

In one embodiment, the carbon source is an autotrophic carbon source and the catalytic component is a bacterium.

In one embodiment, the first incompatible gaseous component is hydrogen, the second incompatible gaseous component is oxygen, the carbon source is carbon dioxide and the bioproduct is IBT. In one embodiment, flow rates of the gaseous reactants are adjusted to minimize wastage and/or excessive accumulation of said gaseous reactants. In one embodiment, flow rates of the gaseous components are adjusted to minimize wastage of the hydrogen and accumulation of the oxygen and the carbon dioxide in the bioreactor. For example, the flow rate of the hydrogen exiting the bioreactor can be adjusted to be lower than a flow rate of the carbon dioxide and/or the oxygen exiting the bioreactor.

Any suitable bioproduct can be produced, such as a biofuel comprising any low carbon chain biofuel, including, but not limited to, isobutanol.

In one embodiment, the bioreactor is part of a system that can include one or more of a separating system or recovery system, such as a biofuel recovery system, including an isobutanol recovery system, and monitoring and control system, and the like.

In one embodiment, the catalytically active zone prevents incompatible gaseous reactants from mixing in the gas-phase while, in one embodiment, simultaneously providing for mass transfer of compatible gaseous reactants in a liquid phase into the catalytically active zone so that the desired chemical reaction can occur.

This approach enables, in one embodiment, construction of a system for the bioreactor to provide, for the first time, not only methods and systems to efficiently convert $CO_2$ and $H_2$ to isobutanol in the presence of $O_2$, but also a suitable device in which the reactions can take place, although other variations are possible as discussed herein.

As such, the various embodiments provide methods that are applicable to a broad swath of biofuel production processes. In one embodiment, new microbial phenotypes are used in a novel hollow-fiber bioreactor that satisfies an unprecedented set of mass transfer, input composition and process stream recycling constraints.

In one embodiment, the ability of engineered *R. eutropha* strains to utilize $CO_2$, $H_2$ and $O_2$ as feedstocks, rather than saccharides, enables the first efficient, scalable conversion of $CO_2$ to infrastructure-ready transportation fuel. In one embodiment, the methods and systems described herein provide a bridge between the forthcoming era of inexpensive, abundant solar-derived $H_2$ and the eventual arrival of a transportation system capable of running on biofuels, such as isobutanol.

Isobutanol can be used without gasoline blending in existing internal combustion engines and is compatible with existing fuel infrastructure. Thus, in one embodiment, isobutanol is an excellent target end product for $H_2$ or electric current-mediated microbial reduction of $CO_2$. In various embodiments, the development of scalable microbial systems for producing isobutanol efficiently from $CO_2$ provides a reduction in fossil fuel dependence and greenhouse gas production without necessitating vehicle modification or the construction of new motor refueling stations.

Although specific embodiments have been illustrated and described herein, it can be appreciated by those of ordinary skill in the art that any procedure that is calculated to achieve the same purpose may be substituted for the specific embodiments shown. This application is intended to cover any adaptations or variations of the present subject matter. For example, although the various embodiments discuss production of isobutanol, other biofuels may be produced, such as other low carbon chain alcohols (e.g., C1-C6), including but not limited to, straight chain alcohols (ethanol and n-butanol) and branched chain alcohols, e.g., isopropanol. Therefore, it is manifestly intended that embodiments of this invention be limited only by the claims and the equivalents thereof.

What is claimed is:

1. A bioreactor for producing a bioproduct comprising:
one or more catalytic component retainers surrounded by a shell side and located within a housing, wherein each of said catalytic component retainers comprises a hollow fiber having a porous fiber wall defining a lumen therein, wherein:
each porous fiber wall is configured to retain a catalytic component within and/or thereon, and to allow a first incompatible gaseous reactant located in a liquid medium within each lumen and a second incompatible gaseous reactant located in a gaseous medium on the shell side to be substantially consumed by the catalytic component and/or wherein
each lumen is configured to contain a liquid medium having a catalytic component located therein and to allow the first incompatible gaseous reactant also located in the liquid medium to be dissolved thereby, further wherein each porous fiber wall is configured to allow the second incompatible gaseous reactant located in a gaseous medium on the shell side to diffuse therethrough and be substantially consumed by the catalytic component, wherein
each porous fiber wall has a pore size distribution and/or an inner skin layer configured to keep first and second incompatible gaseous reactants separated when in the gas phase; and
a microbubble generator operably connected to said catalytic component retainers via an inlet port and configured to generate microbubbles in the liquid medium.

2. The bioreactor of claim 1 further comprising the catalytic component and the liquid medium, wherein the catalytic component is a suspended catalytic component suspended in the liquid medium and each lumen is configured to retain the suspended catalytic component within the liquid medium contained therein such that the liquid medium comprises a catalytically active zone.

3. The bioreactor of claim 2, wherein the gaseous medium and/or the liquid medium are further configured to contain a fermentable carbon source.

4. The bioreactor of claim 3 wherein the fermentation is selected from autotrophic fermentation, heterotrophic fermentation or methanotrophic fermentation.

5. The bioreactor of claim 2 wherein the shell side is a continuous shell side.

6. The bioreactor of claim 2 further comprising:
a cell source to provide the microbial cell culture to the one or more porous fiber walls for inoculation; and
a carbon source to support growth of the microbial cell culture on the one or more porous fiber walls.

7. The bioreactor of claim 6 wherein the carbon source is a heterotrophic carbon source.

8. The bioreactor of claim 6 wherein the microbial cell culture is *Ralstonia eutropha.*

9. The bioreactor of claim 6 further comprising:
a first incompatible gaseous reactant source to provide the first incompatible gaseous reactant to the microbubble generator; and
a second incompatible gaseous reactant source to provide the second gaseous reactant to the gaseous medium.

10. The bioreactor of claim 9 wherein the liquid medium and gaseous medium comprise autotrophic production mediums and the bioreactor further comprises a separating system for separating the bioproduct from the autotrophic production mediums.

11. The bioreactor of claim 9 wherein the gaseous medium comprises methane.

12. The bioreactor of claim 9 wherein the first and second incompatible gaseous reactants have low aqueous solubility.

13. The bioreactor of claim 9 wherein the first incompatible gaseous component contains hydrogen and carbon dioxide, the second incompatible gaseous reactant contains oxygen, and the bioproduct is isobutanol.

14. The bioreactor of claim 9 wherein the first incompatible gaseous component contains hydrogen, the second incompatible gaseous reactant contains oxygen and carbon dioxide, and the bioproduct is isobutanol.

15. The bioreactor of claim 9 further comprising:
the housing; and
a monitoring and control system in communication with the bioreactor.

16. The bioreactor of claim 1 wherein the microbubble generator comprises a spinning disk generator, a swirling-flow generator or an ejector-type generator.

17. The bioreactor of claim 1 wherein the bioreactor further comprises a pump in fluid communication with the microbubble generator.

18. The bioreactor of claim 2 further comprising a surfactant configured to stabilize the microbubbles by imparting an electric double layer.

19. The bioreactor of claim 1 further comprising the catalytic component, wherein the catalytic component and each of said catalytic component retainers comprise a catalytically active zone and the catalytic component is a microbial cell culture located within and/or on the porous fiber wall of each hollow fiber.

20. The bioreactor of claim 1 wherein the pore size distribution is sized to allow cells of the catalytic component to become embedded therein.

21. The bioreactor of claim 2 wherein the catalytic component and each of said catalytic component retainers further comprise a catalytically active zone and the catalytic component further includes a microbial cell culture located within and/or on the porous fiber wall of each hollow fiber.

22. The bioreactor of claim 21 wherein a majority of the catalytic component is the suspended catalytic component.

23. The bioreactor of claim 2 wherein the inner skin layer is located on an inner boundary of each wall and has a pore size distribution sized to prevent cells of the catalytic component from becoming embedded within the porous fiber wall.

24. A bioreactor for producing a bioproduct comprising: one or more catalytic component retainers located within a housing, wherein each of said catalytic component retainers comprises a hollow fiber having a porous fiber wall configured to retain a catalytic component within and/or thereon, wherein each porous fiber wall has a pore size distribution configured to keep the first and second incompatible gaseous reactants separated when in the gas phase, wherein, during operation, the first incompatible gaseous reactant is located in a liquid medium, wherein the liquid medium is located on a first side of each catalytic component retainer, and the second incompatible gaseous reactant is located in a gaseous medium, wherein the gaseous medium is located on a second side of each catalytic component retainer; and a microbubble generator operably connected to the first side of each catalytic component retainer via an inlet port and configured to generate microbubbles in the liquid medium.

25. A method comprising:
producing a bioproduct with a bioreactor comprising one or more catalytic component retainers surrounded by a shell side and located in a housing, wherein each of said catalytic component retainers comprises a hollow fiber having a porous fiber wall defining a lumen therein, wherein
    each porous fiber wall is configured to retain a catalytic component within and/or thereon and to allow a first incompatible gaseous reactant located in a liquid medium within each lumen and a second incompatible gaseous reactant located in a gaseous medium on the shell side to be substantially consumed thereby and/or wherein
    each lumen is configured to contain a liquid medium having a catalytic component located therein and to allow the first incompatible gaseous reactant also located in the liquid medium to be dissolved by the catalytic component, further wherein each porous fiber wall is configured to allow the second incompatible gaseous reactant located in a gaseous medium on the shell side to diffuse therethrough and be substantially consumed by the catalytic component, wherein
    each porous fiber wall has a pore size distribution and/or an inner skin layer configured to keep the first and second incompatible gaseous reactants separated when in the gas phase, and
providing a microbubble generator operably connected to said catalytic component retainers via an inlet port and configured to generate microbubbles in the liquid medium.

* * * * *

UNITED STATES PATENT AND TRADEMARK OFFICE
CERTIFICATE OF CORRECTION

PATENT NO. : 9,714,404 B2
APPLICATION NO. : 14/199714
DATED : July 25, 2017
INVENTOR(S) : Robert Mark Worden and Yangmu Chloe It is certified that error appears in the above-identified patent and that said Letters Patent is hereby corrected as shown below:

In the Specification
Column 2/Line 47: Error reads as "FIG. 21 shows is a" and should read "FIG. 21 shows a"
Column 19/Lines 16-17: Error reads as "(6.1 msec)" and should read as "(6.1 m/sec)"
Column 22/Line 65: Error reads as "software" and should read as "software,"
Column 22/Line 67: Error reads as "Bioreactor" and should read as "Bioreactor."
Column 23/Line 12: Error reads as "that only allowed only" and should read as "that allowed only"
Column 25/Line 17: Error reads as "were them" and should read as "were then"
Column 25/Line 55: Error reads as "entirety" and should read as "entirety."
Column 25/Line 62: Error reads as "layer) at" and should read as "layer at"
Column 26/Line 30: Error reads as "(1.02 atm) After" and should read as "(1.02 atm). After"
Column 26/Line 46: Error reads as "Example 5 In" and should read as "Example 5. In"
Column 27/Line 8: Error reads as "(from" and should read as "from"
Column 27/Line 22: Error reads as "promote microbial cell growth promotes" and should read as "promote microbial cell growth, thus promoting"
Column 27 Lines 29-30: Error reads as "10 m/ml gentamicin" and should read as "Ten (10) µg/ml gentamicin"
Column 30/Line 15: Error reads as "lumen)," and should read as "lumen,"
Column 31/Line 35: Error reads as "velocity and" and should read as "velocity; and"
Column 32/Line 35: Error reads as "indicate an effect" and should read "indicate the effect"
Column 34/Line 67: Error reads as "entirety." and should read as "entirety)."
Column 36/Line 16: Error reads as "mg/(L day)" and should read as "mg/L/day"

In the Claims
Column 42/Claim 25/Line 35: Error reads as "gas phase, and" and should read as "gas phase; and"

Signed and Sealed this
Third Day of October, 2017

Joseph Matal
*Performing the Functions and Duties of the
Under Secretary of Commerce for Intellectual Property and
Director of the United States Patent and Trademark Office*